United States Patent
Maisonneuve et al.

(10) Patent No.: US 9,605,145 B2
(45) Date of Patent: Mar. 28, 2017

(54) PROCESS OF PREPARATION OF POLYOLS AND POLYAMINES, AND PRODUCTS AS OBTAINED

(71) Applicants: CENTRE NATIONAL DE LA RECHERCHE SCIENTIFIQUE (C.N.R.S), Paris (FR); INSTITUT DES CORPS GRAS ETUDES ET RECHERCHES TECHNIQUES—ITERG, Pessac (FR)

(72) Inventors: Lise Maisonneuve, Talence (FR); Thomas Lebarbe, Bordeaux (FR); Henri Cramail, Sainte Terre (FR); Carine Alfos, Pessac (FR); Benoît Gadenne, Le Bouscat (FR); Eric Cloutet, Saint Caprais de Bordeaux (FR)

(73) Assignees: CENTRE NATIONAL DE LA RECHERCHE SCIENTIFIQUE, Paris (FR); INSTITUT DES CORPS GRAS ETUDES ET RECHERCHES TECHNIQUES-ITERG, Pessac (FR)

( * ) Notice: Subject to any disclaimer, the term of this patent is extended or adjusted under 35 U.S.C. 154(b) by 0 days.

(21) Appl. No.: 14/358,078

(22) PCT Filed: Nov. 15, 2012

(86) PCT No.: PCT/EP2012/072785
§ 371 (c)(1),
(2) Date: May 14, 2014

(87) PCT Pub. No.: WO2013/072436
PCT Pub. Date: May 23, 2013

(65) Prior Publication Data
US 2014/0323651 A1    Oct. 30, 2014

(30) Foreign Application Priority Data

Nov. 15, 2011  (EP) .................................... 11306491

(51) Int. Cl.

| | | |
|---|---|---|
| *C07C 323/60* | (2006.01) | |
| *C08L 67/04* | (2006.01) | |
| *C07C 323/52* | (2006.01) | |
| *C08G 63/688* | (2006.01) | |
| *C08G 18/75* | (2006.01) | |
| *C08G 18/38* | (2006.01) | |
| *C08G 69/42* | (2006.01) | |
| *C08G 69/44* | (2006.01) | |
| *C08K 5/37* | (2006.01) | |

(52) U.S. Cl.
CPC ............ *C08L 67/04* (2013.01); *C07C 323/52* (2013.01); *C07C 323/60* (2013.01); *C08G 18/3868* (2013.01); *C08G 18/755* (2013.01); *C08G 63/688* (2013.01); *C08G 63/6886* (2013.01); *C08G 69/42* (2013.01); *C08G 69/44* (2013.01); *C08K 5/37* (2013.01)

(58) Field of Classification Search
CPC ..... C07C 323/52; C07C 323/60; C08G 69/44; C08G 69/42; C08G 63/688; C08G 63/6886; C08G 18/3868
See application file for complete search history.

(56) References Cited

U.S. PATENT DOCUMENTS 3,165,552 A * 1/1965 Dann ...................... G03C 1/09
                                                      430/599
4,551,419 A * 11/1985 Sugimoto ............. C07C 323/25
                                                      430/445
(Continued)

FOREIGN PATENT DOCUMENTS

WO    WO-2010/104167    * 9/2010 ................ C07F 9/09

OTHER PUBLICATIONS

"Unsaturated polyesters based on styrene containing thio-ether bonds: Synthesis, NMR study, characterization of impact and thermal oxidation resistance" Milano et al. Eur. Polym. J. vol. 33, No. 4 pp. 571-576, 1997.*

(Continued)

*Primary Examiner* — Michael L Leonard
(74) *Attorney, Agent, or Firm* — B. Aaron Schulman, Esq.; Stites & Harbison, PLLC.

(57) ABSTRACT

The present invention relates to the use of a compound of formula (I): wherein: —R represents —OH or —$NH_2$; —$A_1$ represents a divalent alkylene radical, straight or branched, having from 2 to 20 carbon atoms; —$A_2$ represents a divalent alkylene radical, straight or branched, having from 1 to 20 carbon atoms; —$X_1$ and $X_2$ represent, independently of each other, —NH— or —O—; —$A_3$ represents a divalent alkylene radical, straight or branched, having from 1 to 10 carbon atoms; —Z represents a hydrogen or a group of formula (A'): wherein $A_1$, $A_3$ and R are as defined above in formula (I), for the preparation of a polymer chosen among polyurethane, polyester and polyamide.

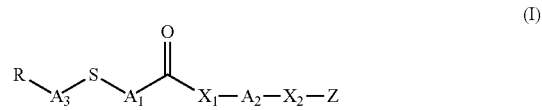

(I)

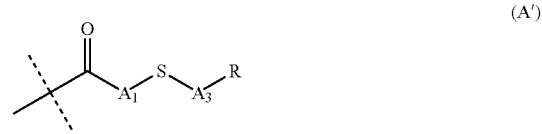

(A')

38 Claims, No Drawings

(56) References Cited

U.S. PATENT DOCUMENTS

| | | | |
|---|---|---|---|
| 6,267,844 B1* | 7/2001 | Jackson | C07C 323/12 162/164.5 |
| 2012/0164905 A1 | 6/2012 | Topolkaraev et al. | |
| 2012/0283467 A1* | 11/2012 | Cramail et al. | 560/154 |

OTHER PUBLICATIONS

Syntheses de diols telecheliques isomoleculaires par telomerisation. Boutevin et al. Makromol. Chem. 191, 445-456 (1990).*

International Search Report for PCT/EP2012/072785 dated Jan. 28, 2013.

B. Boutevin, et al.: "Synthese de diols telecheliques isomoleculaires par telomeisation", Makromolekulare Chemie, vol. 191, No. (Feb. 1990), pp. 445-456.

M.J.P. Vaismaa, et al.: "An improved and green preparation of 3-(alkylthio)propionic acids", Zeitschrift Fur Natruforschung B, vol. 62b, No. 10, (Oct. 2007), pp. 1317-1323.

B. Witten, et al.: "Enzyme-alterable alkylating agents. I. Synthesis, chemical properties, and toxicities of sulfur mustards containing enzyme-susceptible amide bonds", Cancer, vol. 15, No. 5, (Sep. 1962), pp. 1041-1050.

O. Turunk, et al.: "Fatty acid derived monomers and related polymers via thiol-ene(click) additions", Macromolecular Rapid Communications, vol. 31, No. 20, (Oct. 18, 2010), pp. 1822-1826.

* cited by examiner

PROCESS OF PREPARATION OF POLYOLS AND POLYAMINES, AND PRODUCTS AS OBTAINED

The present invention concerns new monomers, such as polyols and polyamines, their process of preparation, and their use for the synthesis of polymers, such as polyurethanes, polyamides and polyesters.

The present invention also concerns new polyurethanes, polyesters and polyamides.

The present invention also concerns the use of the polymers, such as polyurethanes, polyamides and polyesters, for improving the toughness of a polymer matrix, such as a poly(lactic acid) matrix, and/or for enhancing its crystalline ability.

In the literature, the preparation of polyols and polyamines resulting from the petrochemical synthesis is known. However, there is a need to replace petroleum-derived raw materials with renewable ones, especially for an environmental point of view.

Besides, the synthesis of polyols resulting from vegetal oils is known in the literature. However, such known polyols often lead to amorphous linear or cross-linked polymers, having glass transition temperature below ambient temperature.

Thus, there is a need to extend the field of applications of the polyol and polyamine precursors resulting from fatty acids. There is a need to prepare new precursors with a well defined structure, in order to lead to polymers with improved thermo-mechanical properties.

Moreover, the poly(lactic acid) is a polymer having interesting mechanical properties. However, the poly(lactic acid) is a brittle polymer which limits its uses. Indeed, this polymer possesses a low elongation break (about 5%).

In addition, the poly(l-lactic acid) possesses a semi-crystalline feature which is however limited by a very low crystallization rate.

In order to solve this problem, it has been developed incorporation of soft polymers in a poly(lactic acid) matrix. However, it is well know from the state of the art that the use of soft polymers in a poly(lactic acid) matrix leads to incompatibility troubles, and specifically to phase segregation troubles. Besides, most of the soft polymers derive from petrochemicals. Among the soft polymers, mention can be made of poly(butadiene) (Tg=180° C.), poly(propylene oxide) (Tg=−70° C.) or poly(ε-caprolactone) (Tg=−60° C.).

There is still a need to prepare polymers such as polyesters, polyamides or polyurethanes, having improved thermo-mechanical properties compared to the polymers obtained from known monomers derived from vegetal oils.

There is a need to develop new polymers in order to improve the toughness of a brittle polymer matrix, and notably poly(lactic acid) matrix, which do not possess the above-mentioned drawbacks.

There is also a need to develop new polymers which do not result from petroleum derived raw materials.

The aim of the present invention is to provide a new process which consists in a simple and efficient way of chemical modification of fatty acid monoesters for the obtaining of functional and rigid precursors, such as polyols and polyamines.

The aim of the present invention is to provide a simple process of preparation of polyols or polyamines, in only two steps starting with fatty acid monoesters.

Another aim of the present invention is also to provide new precursors, such as polyols and polyamines, with a well defined structure.

The aim of the present invention is to provide polymers, such as polyesters, polyamides and polyurethanes, having good thermo-mechanical properties, from polyol and polyamine precursors.

Another aim of the present invention is to provide polymers for use in numerous applications, such as in the field of fibers, films, foams . . . and in particular in applications with high value-added, especially in the medical or pharmaceutical field.

The aim of the present invention also concerns the use of polymers as additives in a polymer matrix.

Another aim of the present invention is also to provide the use of new precursor monomers for the preparation of additives in a polymer matrix.

The present invention concerns the use of a compound of formula (I):

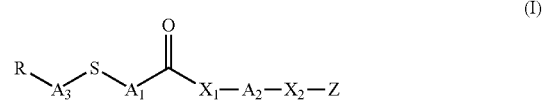

wherein:

R represents —OH or —NH$_2$;

A$_1$ represents a divalent alkylene radical, straight or branched, having from 2 to 20, preferably from 2 to 12 carbon atoms, and optionally comprising at least one double bond, and/or optionally substituted by at least one hydroxyl or amine group;

A$_2$ represents a divalent alkylene radical, straight or branched, having from 1 to 20, preferably from 1 to 10 carbon atoms, and optionally comprising at least one double bond, and/or optionally substituted by at least one hydroxyl or amine group;

X$_1$ and X$_2$ represent, independently of each other, —NH— or —O—;

A$_3$ represents a divalent alkylene radical, straight or branched, having from 1 to 10, preferably from 1 to 5 carbon atoms, and optionally comprising at least one double bond, and/or optionally substituted by at least one hydroxyl or amine group;

Z represents a hydrogen or a group of formula (A'):

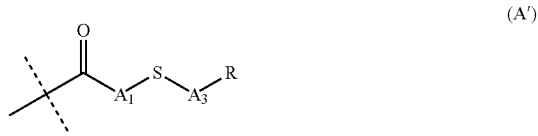

wherein A$_1$, A$_3$ and R are as defined above in formula (I); for the preparation of a polymer chosen among polyurethane, polyester and polyamide.

In particular, the present invention relates to the use of compound of formula (I) as defined above for the preparation of a polymer chosen among polyurethane, polyester and polyamide, being selected from the polymers of formula (VII), (VIII), (IX) and (X) as defined hereafter.

According to an embodiment, in formula (I), A$_1$ represents a straight divalent alkylene radical, having from 3 to 20, preferably from 3 to 12 carbon atoms, and optionally comprising at least one double bond, and/or optionally substituted by at least one hydroxyl or amine group.

According to an embodiment, in formula (I), $A_1$ represents a straight divalent alkylene radical, having from 3 to 20, preferably from 3 to 12 carbon atoms.

According to an embodiment, $A_2$ represents a divalent alkylene radical, straight or branched, having from 3 to 20, preferably from 3 to 10 carbon atoms, and optionally comprising at least one double bond, and/or optionally substituted by at least one hydroxyl or amine group.

According to an embodiment, in formula (I), $A_2$ represents a straight divalent alkylene radical, having from 3 to 20, preferably from 3 to 10 carbon atoms.

According to an embodiment, the present invention concerns the use of a compound having the following formula (I):

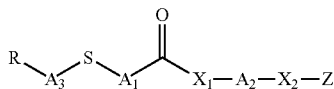

wherein:
R represents —OH or —NH$_2$;
$A_1$ represents a divalent alkylene radical, straight or branched, having from 3 to 20, preferably from 3 to 12 carbon atoms, and optionally comprising at least one double bond, and/or optionally substituted by at least one hydroxyl or amine group;
$A_2$ represents a divalent alkylene radical, straight or branched, having from 3 to 20, preferably from 3 to 10 carbon atoms, and optionally comprising at least one double bond, and/or optionally substituted by at least one hydroxyl or amine group;
$X_1$ and $X_2$ represent, independently of each other, —NH— or —O—;
$A_3$ represents a divalent alkylene radical, straight or branched, having from 1 to 10, preferably from 1 to 5 carbon atoms, and optionally comprising at least one double bond, and/or optionally substituted by at least one hydroxyl or amine group;
Z represents a hydrogen or a group of formula (A'):

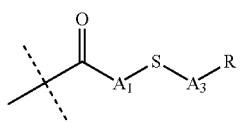

wherein $A_1$, $A_3$ and R are as defined above in formula (I);
wherein when $X_1$ and $X_2$ represent —O—, then R represents —NH$_2$,
for the preparation of a polymer chosen among polyurethane, polyester and polyamide.

According to an embodiment, in formula (I), when R represents OH, then $A_1$ is a straight divalent alkylene radical having from 3 to 20, preferably from 3 to 12 carbon atoms and optionally comprising at least one double bond, and/or optionally substituted by at least one hydroxyl or amine group.

According to an embodiment, the present invention concerns the use as mentioned above of a compound having the formula (I), wherein:

R represents —OH or —NH$_2$;
$A_1$ represents a straight divalent alkylene radical having from 3 to 20, preferably from 3 to 12 carbon atoms;
$A_2$ represents a divalent alkylene radical, straight or branched, having from 3 to 20, preferably from 3 to 10 carbon atoms;
$X_1$ and $X_2$ represent, independently of each other, —NH— or —O—;
$A_3$ represents a divalent alkylene radical, straight or branched, having from 1 to 10, preferably from 1 to 5 carbon atoms;
Z represents a hydrogen or a group of formula (A'):

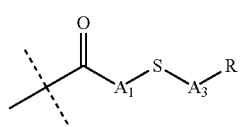

wherein $A_1$, $A_3$ and R are as defined above in formula (I);
wherein when $X_1$ and $X_2$ represent —O—, then R represents —NH$_2$.

According to another embodiment, the present invention concerns the use as defined above of a compound having formula (I), wherein:
R represents —OH or —NH$_2$;
$A_1$ represents a straight divalent alkylene radical having from 3 to 20, preferably from 3 to 12 carbon atoms;
$A_2$ represents a divalent alkylene radical, straight or branched, having from 3 to 20, preferably from 3 to 10 carbon atoms;
$X_1$ and $X_2$ represent, independently of each other, —NH— or —O—;
$A_3$ represents a divalent alkylene radical, straight or branched, having from 1 to 10, preferably from 1 to 5 carbon atoms;
Z represents a hydrogen or a group of formula (A'):

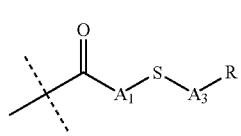

wherein $A_1$, $A_3$ and R are as defined above in formula (I);
wherein when $X_1$ and $X_2$ represent —O—, then R represents —NH$_2$.

In a preferred embodiment, the present invention relates to the use of a compound as defined above having the following formula (I-1):

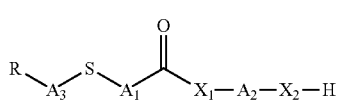

wherein $A_1$, $A_2$, $A_3$, $X_1$, $X_2$ and R being as defined above in formula (I),
wherein the compound of formula (I-1) is preferably chosen from the group consisting of:

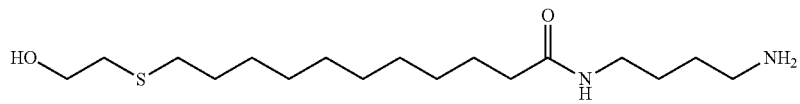

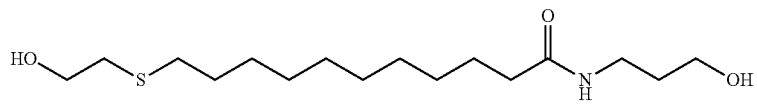

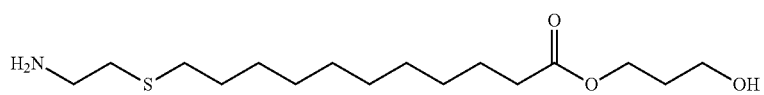

According to an embodiment, the present invention relates to the use as mentioned above of a compound having the following formula (I-2):

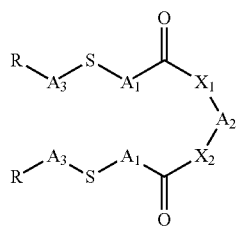
(I-2)

wherein $A_1$, $A_2$, $A_3$, $X_1$, $X_2$ and R being as defined above in formula (I), According to an embodiment, the present invention relates to the use as mentioned above of a compound having the following formula (I-2-1):

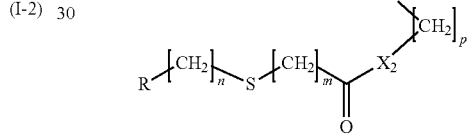
(I-2-1)

wherein:
n is comprised from 1 to 10, preferably from 1 to 5;
m is comprised from 2 to 20, preferably from 5 to 15;
p is comprised from 1 to 20, preferably from 1 to 10; and
R, $X_1$ and $X_2$ are as defined above in formula (I), wherein the compound of formula (I-2-1) is preferably chosen in the group consisting of:

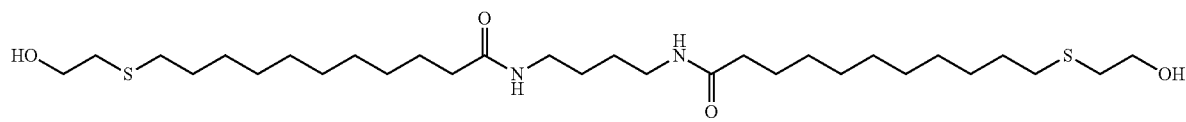

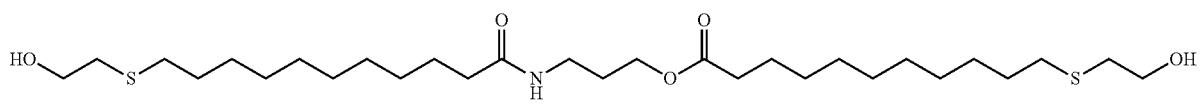

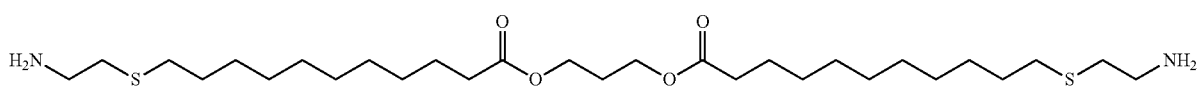

As used herein, the bond wherein the sign ⟋ is present, means that said bond is linked to the $X_2$ atom of the compound of formula (I). Hence, when Z represents a group (A'), then the compound of formula (I) may be written as follows:

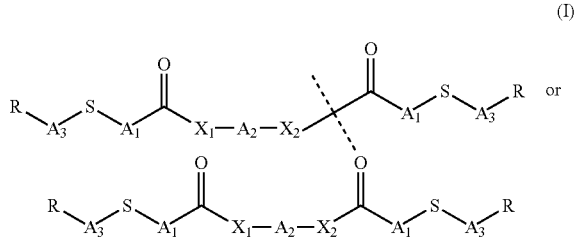

As used herein, the term "alkyl" means a saturated aliphatic hydrocarbon group, which may be straight or branched, having about 1 to about 20 carbon atoms in the chain. Preferred alkyl groups have 1 to about 10 carbon atoms in the chain. The following alkyl groups may be cited as example: methyl, ethyl, propyl, butyl, pentyl, hexyl, heptyl, octyl, nonyl, decyl, dodecyl.

As used herein, the term "alkylene" (or "alkylidene") refers to a divalent radical comprising from 1 to 12 carbon atoms, and preferably from 1 to 6 carbon atoms. When said radical is linear, it may be represented by the formula $(CH_2)_k$ wherein k is an integer varying from 1 to 12, and preferably from 1 to 6.

As used herein, the term "aryl" refers to an aromatic monocyclic or bicyclic hydrocarbon ring system having from 5 to 10 carbons, wherein any ring atom capable of substitution may be substituted by a substituent. Examples of aryl moieties include, but are not limited to, phenyl, naphthyl, and anthracenyl.

As used herein, the term "arylene" (or "arenediyle) refers to a radical derived from arene wherein two hydrogen atoms form the cycle have been deleted. Among the arylene radicals, the o-phenylene radical or the benzene-1,2-diyle may be cited.

As used herein, the term "cycloalkyl" represents a non-aromatic monocyclic or bicyclic ring system having from 4 to 10 carbon atoms. For example, cyclobutyl, cyclopentyle, cyclohexyle, cyclooctyl may be cited.

The present invention also concerns a compound having the following formula (I):

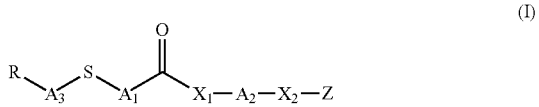

wherein:
R represents —OH or —NH₂;
$A_1$ represents a divalent alkylene radical, straight or branched, having from 2 to 20, preferably from 2 to 12 carbon atoms, and optionally comprising at least one double bond, and/or optionally substituted by at least one hydroxyl or amine group;
$A_2$ represents a divalent alkylene radical, straight or branched, having from 1 to 20, preferably from 1 to 10 carbon atoms, and optionally comprising at least one double bond, and/or optionally substituted by at least one hydroxyl or amine group;
$X_1$ and $X_2$ represent, independently of each other, —NH— or —O—;
$A_3$ represents a divalent alkylene radical, straight or branched, having from 1 to 10, preferably from 1 to 5 carbon atoms, and optionally comprising at least one double bond, and/or optionally substituted by at least one hydroxyl or amine group;
Z represents a hydrogen or a group of formula (A'):

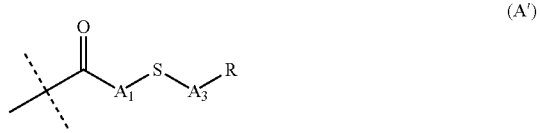

wherein $A_1$, $A_3$ and R are as defined above in formula (I).

According to an embodiment, $A_1$ represents a divalent alkylene radical, straight or branched, having from 3 to 20, preferably from 3 to 12 carbon atoms, and optionally comprising at least one double bond, and/or optionally substituted by at least one hydroxyl or amine group.

According to an embodiment, in formula (I), $A_1$ represents a straight divalent alkylene radical, having from 3 to 20, preferably from 3 to 12 carbon atoms, and optionally comprising at least one double bond, and/or optionally substituted by at least one hydroxyl or amine group.

According to an embodiment, in formula (I), $A_1$ represents a straight divalent alkylene radical, having from 3 to 20, preferably from 3 to 12 carbon atoms.

According to an embodiment, $A_2$ represents a divalent alkylene radical, straight or branched, having from 3 to 20, preferably from 3 to 10 carbon atoms, and optionally comprising at least one double bond, and/or optionally substituted by at least one hydroxyl or amine group.

According to an embodiment, the present invention concerns a compound having the following formula (I):

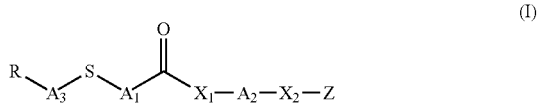

wherein:
R represents —OH or —NH₂;
$A_1$ represents a divalent alkylene radical, straight or branched, having from 3 to 20, preferably from 3 to 12 carbon atoms, and optionally comprising at least one double bond, and/or optionally substituted by at least one hydroxyl or amine group;
$A_2$ represents a divalent alkylene radical, straight or branched, having from 3 to 20, preferably from 3 to 10 carbon atoms, and optionally comprising at least one double bond, and/or optionally substituted by at least one hydroxyl or amine group;
$X_1$ and $X_2$ represent, independently of each other, —NH— or —O—;
$A_3$ represents a divalent alkylene radical, straight or branched, having from 1 to 10, preferably from 1 to 5 carbon atoms, and optionally comprising at least one double bond, and/or optionally substituted by at least one hydroxyl or amine group;

Z represents a hydrogen or a group of formula (A'):

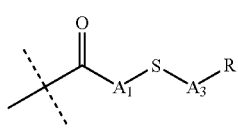

(A')

wherein $A_1$, $A_3$ and R are as defined above in formula (I);

wherein when $X_1$ and $X_2$ represent —O—, then R represents —$NH_2$.

According to an embodiment, in formula (I), when R represents OH, then $A_1$ is a straight divalent alkylene radical having from 3 to 20, preferably from 3 to 12 carbon atoms and optionally comprising at least one double bond, and/or optionally substituted by at least one hydroxyl or amine group.

Preferably, the present invention concerns a compound having the following formula (I):

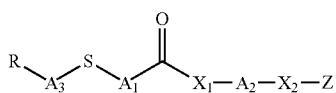

(I)

wherein:

R represents —OH or —$NH_2$;

$A_1$ represents a divalent alkylene radical, straight or branched, having from 3 to 20, preferably from 3 to 12 carbon atoms;

$A_2$ represents a divalent alkylene radical, straight or branched, having from 3 to 20, preferably from 3 to 10 carbon atoms;

$X_1$ and $X_2$ represent, independently of each other, —NH— or —O—;

$A_3$ represents a divalent alkylene radical, straight or branched, having from 1 to 10, preferably from 1 to 5 carbon atoms;

Z represents a hydrogen or a group of formula (A'):

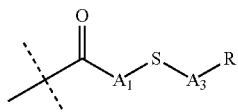

(A')

wherein $A_1$, $A_3$ and R are as defined above in formula (I);

wherein when $X_1$ and $X_2$ represent —O—, then R represents —$NH_2$.

Preferably, the present invention concerns a compound having the following formula (I):

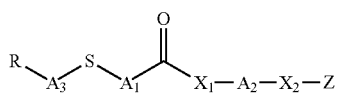

(I)

wherein:

R represents —OH or —$NH_2$;

$A_1$ represents a straight divalent alkylene radical having from 3 to 20, preferably from 3 to 12 carbon atoms;

$A_2$ represents a divalent alkylene radical, straight or branched, having from 3 to 20, preferably from 3 to 10 carbon atoms;

$X_1$ and $X_2$ represent, independently of each other, —NH— or —O—;

$A_3$ represents a divalent alkylene radical, straight or branched, having from 1 to 10, preferably from 1 to 5 carbon atoms;

Z represents a hydrogen or a group of formula (A'):

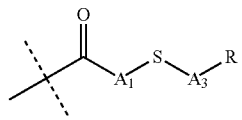

(A')

wherein $A_1$, $A_3$ and R are as defined above in formula (I);

wherein when $X_1$ and $X_2$ represent —O—, then R represents —$NH_2$.

In a preferred embodiment, the present invention relates to a compound having the following formula (I-1):

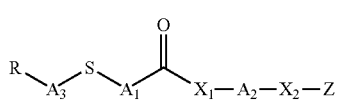

(I)

wherein $A_1$, $A_2$, $A_3$, $X_1$, $X_2$ and R being as defined above in formula (I).

The compounds of formula (I-1) are compounds of formula (I) wherein Z is a hydrogen atom.

In a preferred embodiment, the compounds of formula (I-1) are chosen in the group constituted of:

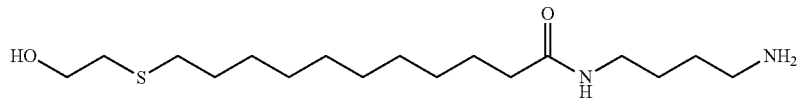

-continued

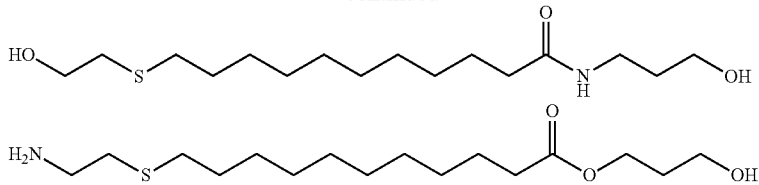

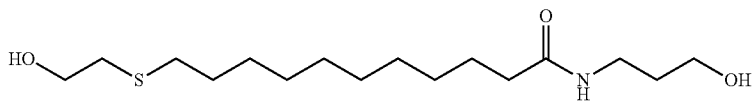 [SMILES: O=C(CCCCCCCCCCSCCO)NCCCO]

In particular, a preferred compound of formula (I-1) is:

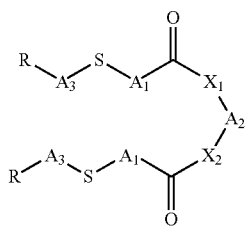

In another embodiment, the present invention relates to a compound having the following formula (I-2):

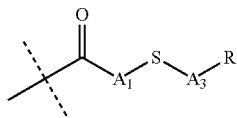

wherein $A_1$, $A_2$, $A_3$, $X_1$, $X_2$ and R being as defined above in formula (I).

The compounds of formula (I-2) are compounds of formula (I) wherein Z represents the group of formula (A'):

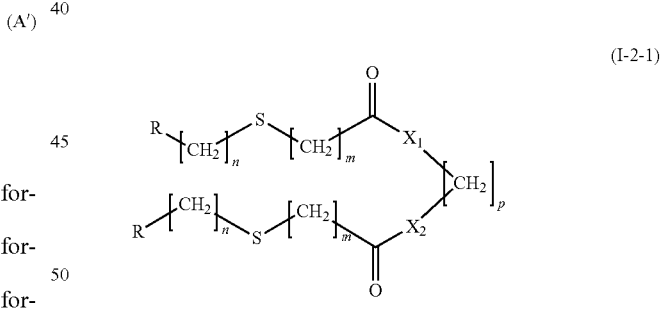

According to an embodiment, in the compounds of formula (I), (I-1) or (I-2), R represents —OH.

According to an embodiment, in the compounds of formula (I), (I-1) or (I-2), R represents —$NH_2$.

According to an embodiment, in the compounds of formula (I), (I-1) or (I-2), $A_3$ represents a divalent alkylene radical, straight or branched, having from 2 to 5 carbon atoms.

In particular, in the compounds of formula (I), (I-1) or (I-2), $A_3$ represents a divalent alkylene radical, straight or branched, having from 2 carbon atoms. In particular, $A_3$ is straight.

According to an embodiment, in the compounds of formula (I), (I-1) or (I-2), $A_1$ represents a divalent alkylene radical, straight or branched, having from 5 to 12 carbon atoms, preferably from 8 to 12 carbon atoms, and optionally comprising at least one double bond, and/or optionally substituted by at least one hydroxyl or amine group. In particular, $A_1$ represents a divalent alkylene radical, straight or branched, having 10 carbon atoms, and more preferably a straight divalent alkylene radical having 10 carbon atoms.

According to an embodiment, in the compounds of formula (I), (I-1) or (I-2), $X_1$ represents —O—.

According to an embodiment, in the compounds of formula (I), (I-1) or (I-2), $X_1$ represents —NH—.

According to an embodiment, in the compounds of formula (I), (I-1) or (I-2), $X_2$ represents —O—.

According to an embodiment, in the compounds of formula (I), (I-1) or (I-2), $X_2$ represents —NH—.

According to an embodiment, in the compounds of formula (I), (I-1) or (I-2), $A_2$ represents a divalent alkylene radical, straight or branched, having from 3 to 8, preferably from 3 to 5 carbon atoms, and optionally comprising at least one double bond, and/or optionally substituted by at least one hydroxyl or amine group. In particular, $A_2$ represents a divalent alkylene radical, straight or branched, having 3 or 4 carbon atoms. Preferably, $A_2$ represents a straight divalent alkylene radical having 3 or 4 carbon atoms.

A family of preferred compounds according to the invention is constituted of compounds having the following formula (I-2-1):

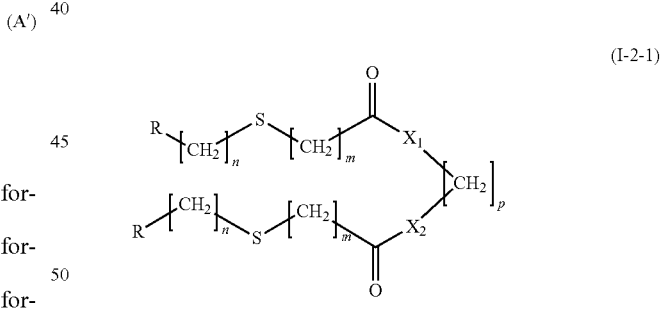

wherein:
n is comprised from 1 to 10, preferably from 1 to 5;
m is comprised from 2 to 20, preferably from 5 to 15;
p is comprised from 1 to 20, preferably from 1 to 10; and
R, $X_1$ and $X_2$ are as defined above in formula (I).

The compounds of formula (I-2-1) are compounds of formula (I-2) wherein $A_3$ represents —$(CH_2)_n$—, $A_1$ represents —$(CH_2)_m$—, $A_2$ represents —$(CH_2)_p$—, and $X_1$ and $X_2$ are independently of each other —NH— or —O—.

According to an embodiment, n is comprised from 1 to 3, preferably n is 2.

According to an embodiment, m is comprised from 6 to 12, preferably from 8 to 12, and more preferably m is 10.

According to an embodiment, p is comprised from 2 to 8, preferably from 3 to 6. In particular, p is 3 or 4.

According to an embodiment, in the compounds of formula (I-2-1), $X_1$ represents —O—.

According to an embodiment, in the compounds of formula (I-2-1), $X_1$ represents —NH—.

According to an embodiment, in the compounds of formula (I-2-1), $X_2$ represents —O—.

According to an embodiment, in the compounds of formula (I-2-1), $X_2$ represents —NH—.

According to an embodiment, in the compounds of formula (I-2-1), R represents —OH.

According to an embodiment, in the compounds of formula (I-2-1), R represents —$NH_2$.

In particular, in formula (I-2-1), n is 2, m is 10, p is 3 or 4, R is —OH or —$NH_2$, and $X_1$ and $X_2$ are independently of each other —NH— or —O—.

Preferably, in formula (I-2-1), n is 2, m is 10, p is 3, R is —OH, $X_1$ is —NH— and $X_2$ is —O—.

Preferably, in formula (I-2-1), n is 2, m is 10, p is 3, R is —$NH_2$, $X_1$ is —O— and $X_2$ is —O—.

Preferably, in formula (I-2-1), n is 2, m is 10, p is 4, R is —OH, $X_1$ is —NH— and $X_2$ is —NH—.

In a preferred embodiment, the compounds of the present invention are chosen in the group constituted of the following compounds:

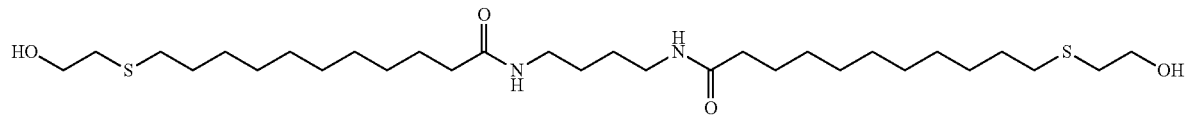

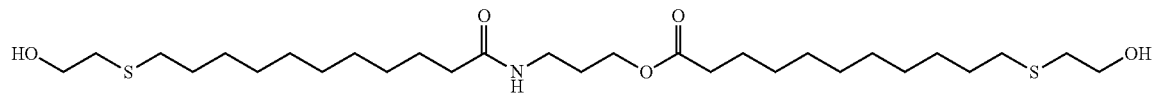

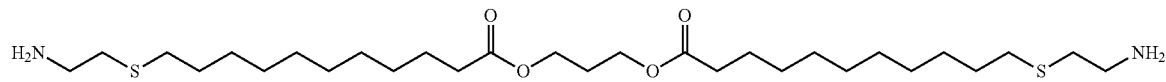

In the present invention, the compounds of formula (I) may be polyols or polyamines. In particular, the compounds of formula (I) are diols or diamines.

According to another aspect, the present invention concerns a process of preparation of the compound of formula (I) as defined above, said process comprising the following steps:

a) a transformation of a compound of formula (II):

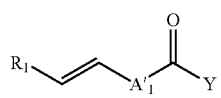

wherein $A'_1$ represents a bond or a divalent alkylene radical, straight or branched, having from 1 to 18 carbon atoms, preferably from 1 to 10, said alkylene radical optionally comprising at least a double bond, and/or optionally substituted by at least one hydroxyl or amine group;

$R_1$ being a hydrogen or an alkyl group, straight or branched, having from 1 to 15 carbon atoms, preferably from 1 to 8;

Y represents —$OR_2$ or —X;

X being a halogen, preferably a chlorine atom;

$R_2$ being a hydrogen, an alkyl group, straight or branched, having from 1 to 10, preferably from 1 to 5 carbon atoms, or a —(C═O)$R_3$, $R_3$ being an alkyl group straight or branched, and having from 1 to 20, preferably from 1 to 10 carbon atoms, and optionally comprising at least one double bond and/or optionally substituted by at least one hydroxyl or amine group;

with a compound of formula (III): H—$X_1$-$A_2$-$X_2$—H (III), $A_2$ being as defined above in formula (I), for obtaining a compound of formula (IV):

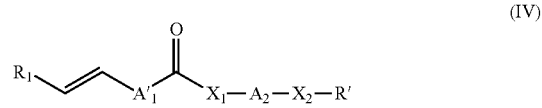

$A'_1$, $A_2$, $X_1$, $X_2$ and $R_1$ being as defined above in formula (I), and R' representing a hydrogen atom or a group of formula (A"):

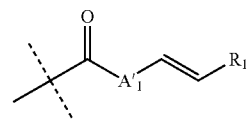

A'$_1$ and R$_1$ being as defined above in formula (II), b) a thiolene reaction of the compound of formula (IV) resulting from step a) as defined above, with a thiol of formula (V):

wherein A$_3$ is as defined above in formula (I), and X$_3$ represents either —OH or —NH$_3^+$ Cl$^-$; and c) optionally a step of basic treatment of the compound resulting from step b); for obtaining the compound of formula (I).

According to an embodiment, the process as defined above provides a compound having the following formula:

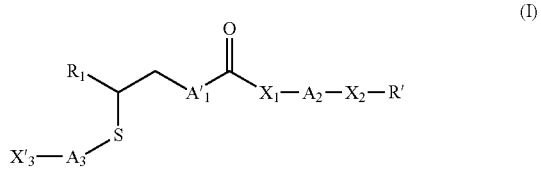

In particular, said compound resulting from the process as defined above, corresponds to a compound of formula (I), wherein:

X'$_3$ corresponds to R;

—CH(R$_1$)—CH$_2$-A'$_1$- corresponds to A$_1$; and

R' corresponds to Z.

In particular, when X$_3$ represents —NH$_3^+$ Cl$^-$ in formula (V), then the process of preparation of compounds of formula (I) comprises a step c), which leads to a compound of formula (I) wherein X'$_3$ (or R) represents —NH$_2$.

In particular, when X$_3$ represents —OH in formula (V), then the process of preparation of compounds of formula (I) does not comprise a step c) and leads to a compound of formula (I) wherein X'$_3$ (or R) represents X$_3$, namely —OH.

According to an embodiment, the basic treatment consists in using a saturated solution of Na$_2$CO$_3$.

According to a preferred embodiment, the step b) consists in reacting the compound of formula (IV) as defined above with 2-mercaptoethanol (compound of formula (V) wherein A$_3$ is an ethyl group and X$_3$ represents —OH).

According to a preferred embodiment, the step b) consists in reacting the compound of formula (IV) as defined above with cysteamine hydrochloride (compound of formula (V) wherein A$_3$ is an ethyl group and X$_3$ represents —NH$_3^+$Cl$^-$).

According to an embodiment, when the step a) is carried out in the presence of an excess of compound of formula (II) compared to compound of formula (III), then R' represents (A'') in the resulting compound of formula (IV). In particular, 2 equivalents of compound of formula (II) are used compared to compound of formula (III).

According to another embodiment, when the step a) is carried out in the presence of an excess of compound of formula (III) compared to compound of formula (II), then R' represents H in the resulting compound of formula (IV). In particular, 2 equivalents of compound of formula (III) are used compared to compound of formula (II).

Preferably, in the compound of formula (II), Y represents —OR$_2$.

In particular, R$_2$ represents a straight alkyl group having from 1 to 10, preferably from 1 to 5 carbon atoms. Preferably, R$_2$ represents methyl.

Preferably, in the compound of formula (II), Y represents —X, and more preferably X represents —Cl.

According to an embodiment, R$_1$ represents H.

According to another embodiment, R$_1$ represents an octyl group.

According to an embodiment, A'$_1$ represents a straight divalent alkylene radical, having from 1 to 18 carbon atoms, preferably from 1 to 10, said alkylene radical optionally comprising at least a double bond, and/or optionally substituted by at least one hydroxyl or amine group. In particular, A'$_1$ represents a straight divalent alkylene radical, having from 2 to 10 carbon atoms, preferably from 5 to 8. In particular, A'$_1$ represents an octyl or heptyl group.

A preferred compound of formula (II) according to the process of the invention is the one wherein R$_1$ represents H, A'$_1$ represents an octyl group and R$_2$ represents H which is undecenoic acid.

A preferred compound of formula (II) according to the process of the invention is the one wherein R$_1$ represents H, A'$_1$ represents an octyl group and R$_2$ represents a methyl group, which is the undecenoate methyl ester.

A preferred compound of formula (II) according to the process of the invention is the one wherein R$_1$ represents an octyl group, A'$_1$ represents a heptyl group and R$_2$ represents H, which is the oleic acid.

A preferred compound of formula (II) according to the process of the invention is the one wherein R$_1$ represents an octyl group, A'$_1$ represents a heptyl group and R$_2$ represents a methyl group, which is the oleate methyl ester.

A preferred compound of formula (II) according to the process of the invention is the one wherein R$_1$ represents an octyl group which comprises an hydroxyl group on the seventh carbon atom, A'$_1$ represents a heptyl group and R$_2$ represents H, which is the ricinoleic acid.

A preferred compound of formula (II) according to the process of the invention is the one wherein R$_1$ represents an octyl group which comprises an hydroxyl group on the seventh carbon atom, A'$_1$ represents a heptyl group and R$_2$ represents a methyl group, which is the ricinoleate methyl ester.

According to the process of the present invention, the transformation of the step a) may be of different nature, depending on the nature of the compounds of formulae (II) and (III).

More particularly, when Y represents —OR$_2$, and when R$_2$ represents an alkyl group in formula (II), the transformation of the step a) may be one of the following reactions, depending on the nature of the compound of formula (III):

(i) if X$_1$ and X$_2$ represent —NH— in the compound of formula (III), then the transformation of step a) is an transamidification of the ester functions of the compound of formula (II);

(ii) if X$_1$ and X$_2$ represent —O— in the compound of formula (III), then the transformation of step a) is a transesterification of the ester functions of the compound of formula (II);

(iii) if X$_1$ represents —NH— and X$_2$ represents —O— in the compound of formula (III), then the transformation of step a) is both an transamidification and a transesterification of ester functions of compound of formula (II). More particularly, the reaction of transamidification of one ester function of compound of formula (II) may be performed with a moiety of compound of formula (III) wherein X$_1$ represents —NH—, and the transesterification of a second ester function of compound of formula (III) may be performed with the other moiety of compound of formula (III) wherein $X_2$ represents —O—.

In another embodiment, when Y represents —OR$_2$ and when R$_2$ represents a hydrogen atom in formula (II), the transformation of the step a) may be one of the following reactions, depending on the nature of the compound of formula (III):
  (i) if $X_1$ and $X_2$ represent —NH— in the compound of formula (III), then the transformation of step a) is an amidification of the acid functions of the compound of formula (II);
  (ii) if $X_1$ and $X_2$ represent —O— in the compound of formula (III), then the transformation of step a) is an esterification of the acid functions of the compound of formula (II);
  (iii) if $X_1$ represents —NH— and $X_2$ represents —O— in the compound of formula (III), then the transformation of step a) is both an amidification and an esterification of acid functions of compound of formula (II). More particularly, the reaction of amidification of one acid function of compound of formula (II) may be performed with a moiety of compound of formula (III) wherein $X_1$ represents —NH—, and the esterification of a second acid function of compound of formula (III) may be performed with the other moiety of compound of formula (III) wherein $X_2$ represents —O—.

In another embodiment, when Y represents —X in formula (II), X being a halogen, and more preferably X being a chlorine atom, the transformation of the step a) may be a substitution reaction.

As used herein, the term "transamidification" means a chemical reaction that consists of reacting a mono- or di-amine with an ester to form a mono-amide compound (if a mono-amine is used) or a di-amide compound (if a di-amine is used).

As used herein, the term "amidification" means a chemical reaction that consists of reacting a mono- or di-amine with an acid function of a compound to form a mono-amide compound (if a mono-amine is used) or a di-amide compound (if a di-amine is used).

As used herein, the term "transesterification" means a chemical reaction that consist of reacting a mono-alcohol or diol with an ester function of compound to form a mono-ester compound (if a mono-alcohol is used) or a di-ester compound (if a diol is used).

As used herein, the term "esterification" means a chemical reaction that consists of reacting a mono-alcohol or diol with an acid function of a compound to form a mono-ester compound (if a mono-alcohol is used) or a di-ester compound (if a diol is used).

As used herein, the term "substitution" corresponds to the replacement of the halogen atom, in the compound of formula (II) wherein Y represents X, X preferably being a chlorine atom, resulting from the reaction of a mono-alcohol (or diol) or a monoamine (or diamine) with the carbonyl bearing the halogen atom.

According to an embodiment, the compound of formula (I) may possess either:
  an amide linkage if the step a) is a transamidification or an amidification; or
  an ester linkage if the step a) is a transesterification; or
  both an amide and an ester linkage if the step a) consists of a mixed transamidification/transesterification or mixed amidification/esterification.

In a preferred embodiment, the compound of formula (III) involved in the process of the present invention is selected from the group consisting of:

(III-1)

(III-2)

(III-3)

In particular, in the process of preparation of compound of formula (I) as defined above, when the compound (III-1) is used, and when Y represents —OR$_2$ in formula (II), the transformation of the step a) is an amidification or a transamidification. Preferably, the transformation of the step a) is a transamidification.

In particular, in the process of preparation of compound of formula (I) as defined above, when the compound (III-2) is used, and when Y represents —OR$_2$ in formula (II), the transformation of the step a) is both an amidification or transamidification carried out with the amino moiety of compound (III-2) and a transesterification or esterification carried out with the hydroxyl moiety of compound (III-2). Preferably, the transformation of step a) is both an transamidification and a transesterification.

In particular, in the process of preparation of compound of formula (I) as defined above, when the compound (III-3) is used, and when Y represents —OR$_2$ in formula (II), the transformation of the step a) is a transesterification or an esterification. Preferably, the transformation of the step a) is a transesterification.

In another embodiment, the compound of formula (I) may possess either:
  an amide linkage if the step a) is a substitution carried out with the compound (III-1);
  an ester linkage if the step a) is a substitution carried out with the compound (III-3);
  both an amide and an ester linkage if the step a) consists of a substitution carried out with the compound (III-2).

According to the invention, following the first step of amidification or transamidification and/or transesterification or esterification (step a)), a second step is necessary to introduce further hydroxyl or amine functions (step b)). Thus, the thiolene reaction allows grafting a primary hydroxyl or a primary amine via a thiol function (step b) as mentioned above.

According to one embodiment, the present invention also concerns a process as defined above, for the preparation of the compound of formula (I-1):

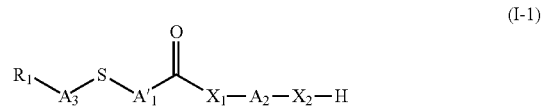
(I-1)

wherein $A_1$, $A_2$, $A_3$, $X_1$, $X_2$ and R being as defined above in formula (I), wherein the step a) of said process leads to a compound of formula (IV) wherein R' represents H.

According to another embodiment, the present invention concerns a process as defined above, for the preparation of the compound of formula (I-2):

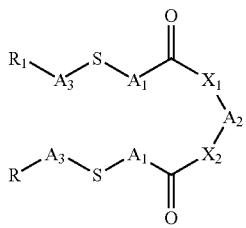
(I-2)

$A_1$, $A_2$, $A_3$, $X_1$, $X_2$ and R being as defined above in formula (I), wherein the step a) of said process leads to a compound of formula (IV) as defined above, wherein R' represents the group of formula (A"):

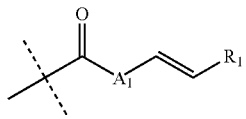

$A_1$ and $R_1$ being as defined in formula (I).

According to an embodiment, the present invention concerns a process as defined above, for the preparation of the compound of formula (I-2-1):

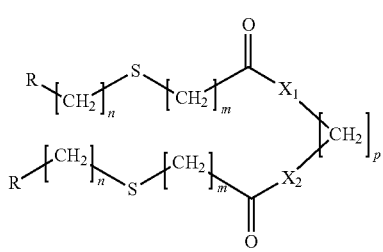
(I-2-1)

wherein:
n is comprised from 1 to 10, preferably from 1 to 5;
m is comprised from 2 to 20, preferably from 5 to 15;
p is comprised from 1 to 20, preferably from 1 to 10; and
R, $X_1$ and $X_2$ are as defined above in formula (I).

In a preferred embodiment, the step a) is carried out in presence of a catalyst chosen in the group consisting of: 1,5,7-triazabicyclo[4.4.0]dec-5-ene (TBD), Zn(OAc)$_2$ and Ti(OR)$_4$.

Preferably, the catalyst is 1,5,7-triazabicyclo[4.4.0]dec-5-ene (TBD). Typically, the catalyst may be used from 1 to 10% molar, preferably from 2 to 6% molar. Preferably, the catalyst is used at 5% molar.

In another embodiment, the step a) of the process of the invention may be carried out without catalyst.

In a preferred embodiment, the transformation of step a) of the process is carried out at a temperature comprised from 100° C. to 200° C., preferably from 120° C. to 160° C., under nitrogen flux for several hours.

In a preferred embodiment, the transformation of step a) is carried out for 4 hours at 120° C. and then for 2 hours at 160° C.

In a preferred embodiment, the transformation of step a) is carried out for 2 hours at 150° C. and then for 2 hours at 160° C.

According to a preferred embodiment, the transformation of step a) may be carried out without the use of solvent, which is advantageous in the field of green chemistry.

According to a preferred embodiment, the thiolene reaction of step b) is a radical addition reaction carried out under UV irradiations or in presence of a radical initiator, such as azobisisobutyronitrile (AIBN).

Typically, the thiolene reaction may be carried out in presence of 1 to 20 equivalents of compound of formula (V) as defined above, per double bond of the compound of formula (IV) as defined above. Preferably, 6 to 12 equivalents are used.

In one embodiment, when $X_1$ and $X_2$ represent —NH— in the formula (III) as defined above, then the thiolene reaction of step b) is carried out in presence of a radical initiator, such as azobisisobutyronitrile (AIBN).

In another embodiment, when $X_1$ represents —NH— or —O— and $X_2$ represents —O— in the formula (III) as defined above, then the thiolene reaction is carried out under UV irradiations. Preferably, the reaction of step b) is carried out at 254 nm or 365 nm.

Typically, the thiolene reaction may be carried out at a temperature comprised from 0° C. to 100° C., preferably from 20° C. to 80° C., for several hours.

Typically, the thiolene reaction may be carried out in a solvent chosen among: dichloromethane, dioxane, ethanol, N-methyl-pyrrolidone (NMP), tetrahydrofuran, dimethylformamide (DMF), or a mixture of them. Preferably, the solvent used is dichloromethane, a mixture dioxane/ethanol (70/30) or NMP.

In the present invention, new polyol or polyamine synthons derived from renewable resources have been advantageously synthesized.

As used herein, the term "polyol or polyamine synthons" also refers to "precursors" for the preparation of polyamides, polyesters or polyurethanes or to "polyol or polyamine building blocks" or to "monomers".

The structures of the polyols or polyamines synthons obtained according to the process of the present invention are interesting due to the presence of terminal primary amine or primary hydroxyl functions. Indeed, the obtained polyols and polyamines are advantageously highly functional precursors with controlled functionality. It is interesting to control the functionality of the polyol or polyamine synthons for the preparation of polymers with reproducible and controlled properties. For example, the use of polyol or polyamine synthons exhibiting a functionality of 2 allows leading to linear polymers, whereas the use of synthons with higher functionality, can lead to branched polymers.

The monomers of formula (I) obtained according to the invention, advantageously possess a great rigidity, which make them potential precursors for the preparation of original polymers. Such rigidity results notably from the presence of amide linkages.

The resulting polyols or polyamines synthons of the present invention possess advantageously great thermomechanical properties. They may be crystalline compounds with high melting point.

The present invention also concerns a polymer, in particular a polyurethane, susceptible to be obtained by polymerization of the compound of formula (I) as defined above, and of a polyisocyanate.

According to an embodiment, the polyisocyanate is a diisocyanate, and preferably a diisocyanate of formula (O)CN-$A_4$-NC(O), wherein $A_4$ represents:
- an alkylene radical, straight or branched, having from 2 to 20 carbon atoms; or
- a cycloalkylene-alkylene-cycloalkylene radical, having from 6 to 30 carbon atoms; or
- a arylene-alkylene-arylene radical, having from 6 to 30 carbon atoms; or
- a cycloalkylene radical, having from 3 to 10 carbon atoms; or
- a alkylene-cycloalkylene, having from 3 to 15 carbon atoms; or
- an arylene radical, having from 6 to 10 carbon atoms.

wherein the alkylene, cycloalkylene and arylene radicals are optionally substituted by at least one substituent selected from the group constituted of: alkyl, aryl and cycloalkyl.

According to an embodiment, $A_4$ represents an alkylene-cycloalkylene, wherein the cycloalkylene is substituted by at least one alkyl group, and preferably by three alkyl groups.

According to an embodiment, $A_4$ represents an arylene-alkylene-arylene.

Preferably, the diisocyanate is isophorone diisocyanate (IPDI) or diphenylmethane 4,4'-diisocyanate (MDI).

According to the invention, the polymer susceptible to be obtained by polymerization of the compound of formula (I) and of a polyisocyanate as defined above, may have the following formula (VII):

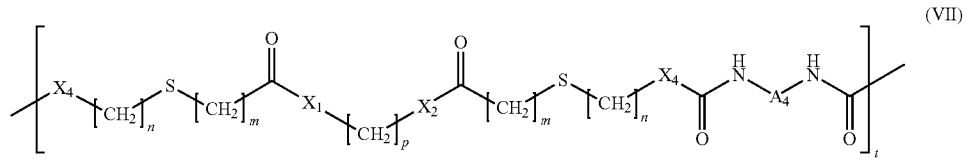

wherein:
- n, m and p are as defined above in formula (I-2-1);
- $X_1$ and $X_2$ are as defined above in formula (I);
- $A_4$ is as defined above;
- $X_4$ represents —NH— or —O—; and
- t represents a integer comprised from 1 to 50000, preferably from 1 to 5000, and more preferably from 1 to 50.

Preferably, the polymer susceptible to be obtained by polymerization of a compound of formula (I) and of IPDI, as polyisocyanate as defined above, has the following formula (VII-1):

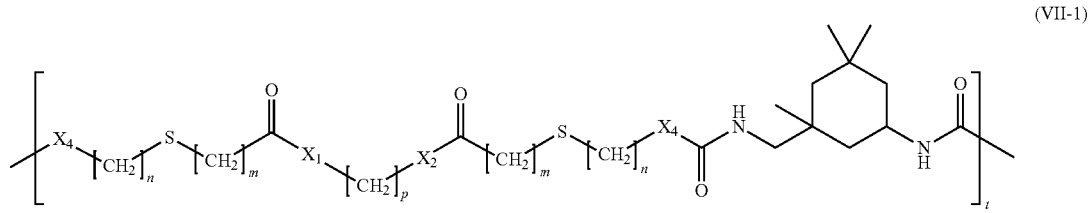

wherein n, m, p, $X_1$, $X_2$, $X_4$ and t are as defined above in formula (VII).

Preferably, the polymer susceptible to be obtained by polymerization of a compound of formula (I) and of MDI, as polyisocyanate as defined above, has the following formula (VII-2):

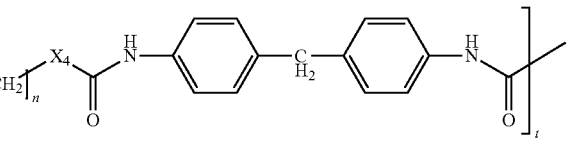

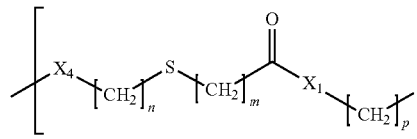

wherein n, m, p, $X_1$, $X_2$, $X_4$ and t are as defined above in formula (VII).

According to the invention, the polymers of formulae (VII), (VII-1) and (VII-2) may possess different terminal moieties, depending on the stoechiometry of the reactants used for the preparation of said polymers.

For example, if a diisocyanate of formula (O)CN-$A_4$-NC(O) is used in large excess compared to the compound of formula (I-2-1), then the polymer comprises isocyanate functions as terminal moieties.

For example, if a compound of formula (I-2-1) is used in large excess compared to diisocyanate of formula (O)CN-$A_4$-NC(O), then the polymer has —OH or —$NH_2$ as terminal moieties.

For example, the polymer may also contain different terminal moieties on the polymer, namely an isocyanate function at one end of the polymer and a —OH or —$NH_2$ at the other end of the polymer.

According to an embodiment, in the polymers of formula (VII), (VII-1) or (VII-2), n is comprised from 1 to 5. In particular, n is 2.

According to an embodiment, in the polymers of formula (VII), (VII-1) or (VII-2), m is comprised from 8 to 12. In particular, m is 10.

According to an embodiment, in the polymers of formula (VII), (VII-1) or (VII-2), p is comprised from 3 to 6. In particular, p is 3 or 4.

According to an embodiment, in the polymers of formula (VII), (VII-1) or (VII-2), $X_1$ represents —O—.

According to an embodiment, in the polymers of formula (VII), (VII-1) or (VII-2), $X_1$ represents —NH—.

According to an embodiment, in the polymers of formula (VII), (VII-1) or (VII-2), $X_2$ represents —O—.

According to an embodiment, in the polymers of formula (VII), (VII-1) or (VII-2), $X_2$ represents —NH—.

According to an embodiment, in the polymers of formula (VII), (VII-1) or (VII-2), t is comprised from 2 to 50000, in particular from 10 to 1000, and preferably from 20 to 80.

According to an embodiment, in the polymers of formula (VII), (VII-1) or (VII-2), $X_4$ represents —O—.

According to an embodiment, in the polymers of formula (VII), (VII-1) or (VII-2), $X_4$ represents —NH—.

Preferred polymers according to the invention, are those for which in formulae (VII), (VII-1) or (VII-2) as defined above, $X_4$ represents —O—, $X_1$ and $X_2$ represent —NH—, n represents 2, m represents 10 and p represents 4.

Preferred polymers according to the invention, are those for which in formulae (VII), (VII-1) or (VII-2) as defined above, $X_4$ represents —O—, $X_1$ represents —NH—, $X_2$ represents —O—, n represents 2, m represents 10 and p represents 3.

Preferred polymers according to the invention, are those for which in formulae (VII), (VII-1) or (VII-2) as defined above, $X_4$ represents —NH—, $X_1$ and $X_2$ represent —O—, n represents 2, m represents 10 and p represents 3.

The present invention also concerns a polymer, in particular a polyester, susceptible to be obtained by polymerization of the compound of formula (I) as defined above, and of a polyester (different from the polyester resulting of the polymerization step).

According to an embodiment, the polyester is a diester, and preferably a diester of formula (VI):

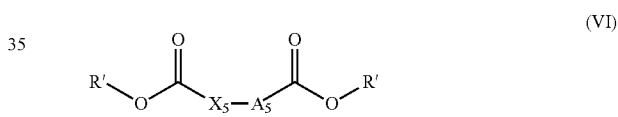

wherein:
R' represents H, an alkyl group having from 1 to 10 carbon atoms, or —(C═O)$R_3$, $R_3$ being an alkyl group straight or branched, and having from 1 to 20, preferably from 1 to 10 carbon atoms, and optionally comprising at least one double bond and/or optionally substituted by at least one hydroxyl or amine group;
$X_5$ represents —$CH_2$— or —$CH_2S$—;
$A_5$ represents an alkylene radical, straight or branched, having from 1 to 12 carbon atoms, said alkylene radical being eventually substituted by an alkyl group having from 1 to 10 carbon atoms, and said alkylene radical eventually comprising a double bond.
Preferably, the diester of formula (VI) is chosen among:

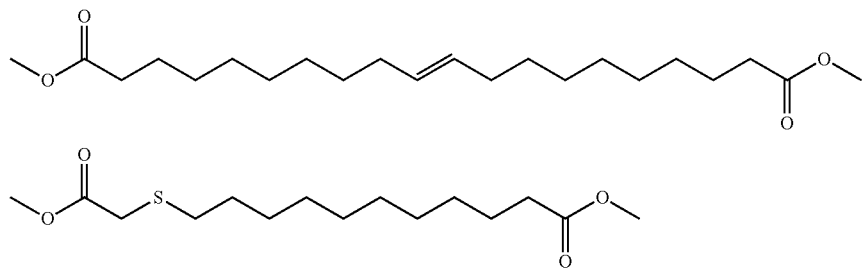

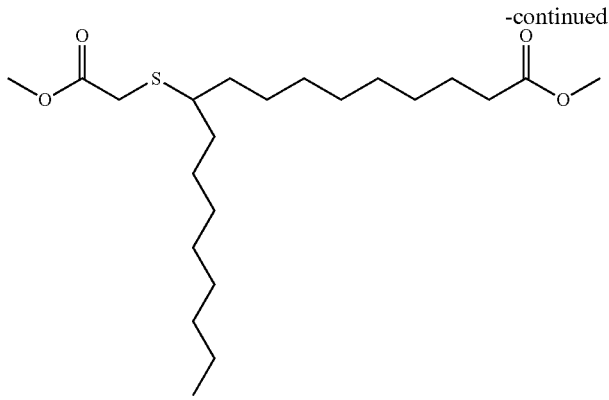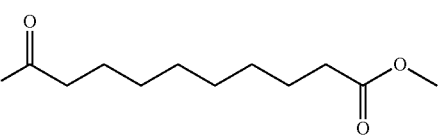

According to the invention, the polymer susceptible to be obtained by polymerization of the compound of formula (I) and of a polyester has defined above, may have the following formula (VIII):

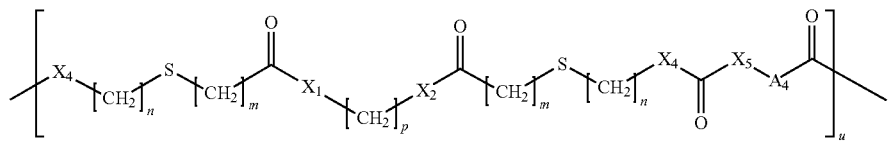

wherein:
- n, m and p are as defined above in formula (I-2-1);
- $X_1$ and $X_2$ are as defined above in formula (I);
- $A_5$ and $X_5$ are as defined above in formula (VI);
- $X_4$ represents —NH— or —O—;
- u represents a integer comprised from 1 to 50000, preferably from 1 to 5000, and more preferably from 1 to 50.

According to the invention, the polymers of formula (VIII) may possess different terminal moieties, depending on the stoechiometry of the reactants used for the preparation of said polymers.

For example, if a compound of formula (VI) is used in large excess compared to the compound of formula (I-2-1), then the polymer has ester (acide or anhydride) functions as terminal moieties.

For example, if a compound of formula (I-2-1) is used in large excess compared to the compound of formula (VI), then the polymer has —OH or –NH$_2$ as terminal moieties.

For example, the polymer may also contain different terminal moieties on the polymer, namely an ester (acid or anhydride) function at one end of the polymer and a —OH or —NH$_2$ at the other end of the polymer.

According to an embodiment, in formula (VIII), $X_4$ represents —O—.

According to an embodiment, in formula (VIII), $X_1$ represents —NH—.

According to an embodiment, in formula (VIII), $X_2$ represents —NH—.

According to an embodiment, in formula (VIII), n is comprised from 1 to 5. In particular, n is 2.

According to an embodiment, in formula (VIII), m is comprised from 8 to 12. In particular, m is 10.

According to an embodiment, in formula (VIII), p is comprised from 3 to 6. In particular, p is 4.

According to an embodiment, in formula (VIII), $X_5$ represents —CH$_2$—.

According to an embodiment, in formula (VIII), $X_5$ represents —CH$_2$S—.

According to an embodiment, in formula (VIII), $A_5$ represents a C17 alkyl group comprising a double bond, preferably between the 8$^{th}$ and the 9$^{th}$ carbon atoms of the alkyl chain.

According to an embodiment, in formula (VIII), $A_5$ represents a C10 alkyl group or a C7 alkyl group.

According to an embodiment, in formula (VIII), $A_5$ represents a C9 alkyl group, substituted by a C8 alkyl group, preferably on the first carbon atom of the alkyl chain.

According to an embodiment, in formula (VIII), u is comprised from 2 to 50000, preferably from 10 to 50.

Preferred polymers according to the invention are those for which in formula (VIII), as defined above, $X_4$ represents —O—, $X_1$ and $X_2$ represent —NH—, n represents 2, m represents 10, p represents 4, $X_5$ represents —CH$_2$— and $A_5$ represents a C17 alkyl group comprising a double bond, preferably between the 8$^{th}$ and the 9$^{th}$ carbon atoms of the alkyl chain.

Preferred polymers according to the invention are those for which in formula (VIII), as defined above, $X_4$ represents —O—, $X_1$ and $X_2$ represent —NH—, n represents 2, m represents 10, p represents 4, $X_5$ represents —CH$_2$S— and $A_5$ represents a C10 alkyl group.

Preferred polymers according to the invention are those for which in formula (VIII), as defined above, $X_4$ represents —O—, $X_1$ and $X_2$ represent —NH—, n represents 2, m represents 10, p represents 4, $X_5$ represents —CH$_2$S— and $A_5$ represents a C9 alkyl group, substituted by a C8 alkyl group, preferably on the first carbon atom of the alkyl chain.

Preferred polymers according to the invention are those for which in formula (VIII), as defined above, $X_4$ represents —O—, $X_1$ and $X_2$ represent —NH—, n represents 2, m represents 10, p represents 4, $X_5$ represents —CH$_2$— and $A_5$ represents a C7 alkyl group.

According to the invention, the structure of the polyisocyanate, notably diisocyanate, has an impact on the nature and properties of the resulting polyurethane. Indeed, according to the structure of the polyisocyanate used, the obtained polyurethane possesses different thermo-mechanical properties, such as a crystallization rate, glass transition temperature or melting temperature. For example, the use of a symmetric polyisocyanate, such as MDI, may lead to linear polyurethane with high melting temperature and high glass transition temperature, whereas the use of a non symmetric polyisocyanate, such as IPDI, may lead to a polyurethane which crystallizes at lower temperature contrary to symmetric polyisocyanate. Thus there is a selectivity of the functionality of the polyurethane according to the nature of the polyisocyanate.

Similarly, according to the invention, the nature of the polyester, notably the diester, may have an impact on the properties and nature of the resulting polyester. Hence, by modulating the nature of the diester, the melting temperature and the glass transition temperature of the resulting polyester vary. In the present invention, it has been shown that the use of the most symmetric and the shortest diester, leads to polyester with the highest glass transition temperature and melting temperature. Besides, the use of a diester having a substituent such as an alkyl chain, which makes the diester less linear, leads to a polyester having lower glass transition temperature.

According to the invention, the nature of the compounds of formula (I), which are precursors for the preparation of polymers, such as polyurethanes, polyesters and polyamides, may also have an impact on nature and thermo-mechanical properties of the resulting polymers. It has been found that the use of linear monomer (compound of formula (I)), favours the crystallization of the polymer, whereas the use of branched monomers does not favour such crystallization.

According to an embodiment, the present invention concerns polyamides, susceptible to be obtained by polymerization of the compound of formula (I) as defined above, wherein R represents —NH$_2$, with a diester or a diacid.

Preferably, the present invention concerns polyamides, susceptible to be obtained by polymerization of the following compound of formula (I):

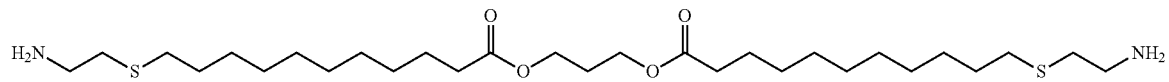 [SMILES: NCCSCCCCCCCCCCC(=O)OCCCOC(=O)CCCCCCCCCCSCCN]

with a diester or a diacid.

According to the invention, the use of compound of formula (I) wherein R represents —NH$_2$, allows the formation of amide bonds in the resulting polyamides, due to the reaction of the —NH$_2$ groups of compound of formula (I) with a diester or a diacid. Such amide bonds may confer rigidity of the resulting polyamide.

The present invention also concerns a process of preparation of polyurethane having one of the following formulae (VII), (VII-1) or (VII-2), comprising a step of reacting a compound of formula (I) as defined above with a diisocyanate of formula (O)CN-A$_4$-NC(O) as defined above, at a temperature comprised from 40° C. to 100° C., preferably from 80° C. to 90° C., in a solvent, such as DMF.

Typically, the reaction may be carried out with or without the use of a catalyst.

Preferably, if the reaction is carried out with IPDI as diisocyanate, dibutyl tin dilaurate (DBTDL) is used as catalyst in a quantity comprised from 0.01% to 0.9%, preferably from 0.05% to 0.20% by weight, compared to the total weight of the reagents.

Preferably, if the reaction is carried out with MDI as diisocyanate, no catalyst is necessary.

Typically, the formation of the polyurethanes according to the invention may be confirmed by FTIR-ATR analysis, thanks to the disappearance of the specific vibration bands of the isocyanate functions and the appearance of those of the urethane functions.

According to an other aspect, the present invention concerns a process of preparation of polyester having the formula (VIII), comprising a step of reacting a compound of formula (I) as defined above with a diester of formula (VI) as defined above, at a temperature comprised from 100° C. to 200° C., preferably from 130° C. to 190° C.

Typically, the reaction may be carried out in presence of a catalyst. Preferably, TBD, or Ti(BuO)$_4$, is used as catalyst in a quantity comprised from 1 to 20% molar, preferably from 5 to 10% molar.

Preferably, the reaction is carried out under nitrogen flux or under dynamic vacuum.

In the present invention, polymers, such as polyurethanes, polyesters and polyamides, resulting from bio-sourced monomers, such as polyols or polyamines, have been prepared. It was advantageously shown that the use of the bio-sourced monomers according to the invention allows modulating and improving the thermo-mechanical properties of the resulting polymers, such as polymers of formulae (VII) and (VIII).

Hence, the use of the compounds of formula (I) according to the invention, allows obtaining polymers having semi-crystallinity properties. The obtained polymers, such as polyesters, polyurethanes or polyamides, according to the invention, in particular polymers of formulae (VII) and (VIII), advantageously exhibit high glass transition temperature (Tg) and high melting points opening various opportunities for industrial applications.

It was also shown that the structures of the polyisocyanate and of the monomers of formula (I) used for the preparation of polyurethanes have an impact on the thermo-mechanical properties of the resulting polymers. Hence, the use of symmetrical polyisocyanates, as well as the use of linear monomers, leads to more crystalline polyurethanes, in particular polyurethanes of formula (VII), which exhibit high glass transition temperature and high melting points. The same phenomenon was observed for the preparation of polyesters and polyamides.

Besides, it was interestingly shown that the use of the original monomers leads to hybrid polymers such as poly (ester-amide)s and poly(urethane-amide)s and poly(amide-ester)s composed of both ester and amide linkages or urethane and amide linkages.

The present invention also relates to the use of the polymers as defined above, preferably polymers of formula (VII) or (VIII), for the preparation of adhesives, surfactants, coatings, packing, paints, fibers, foams, as well as in the cosmetic or medical fields.

The present invention also concerns a polymer, susceptible to be obtained by polymerization of the compound of formula (I) as defined-above, and of a diacid derivative chosen from diacid, diester or dianhydride compounds.

According to an embodiment, the diacid derivative has the following formula (XI):

R'''OOC—R''—COOR''' (XI)

wherein R'' represents:
- an alkylene radical, straight or branched, having from 1 to 30, preferably from 2 to 20, carbon atoms; or
- an alkylene-cycloalkylene-alkylene radical, having from 6 to 50 carbon atoms, preferably from 12 to 36 carbon atoms; or
- a cycloalkylene radical having from 6 to 30 carbon atoms, an arylene radical having from 6 to 30 carbon atoms; or
- a polymer;

wherein R''' represents H, an alkyl group as defined above or an anhydride group (COAlk, Alk representing an alkyl group as defined above), wherein the alkylene, cycloalkylene and arylene radicals are:
- optionally substituted by at least one substituent selected from the group constituted of: alkyl, aryl and cycloalkyl; and/or
- optionally interrupted with at least one heteroatom chosen from the group consisting in: O, N and S.

According to an embodiment, the present invention relates to a polymer susceptible to be obtained by polymerization of the compound of formula (I) as defined-above, and of a diacid having the following formula (XI):

HOOC—R''—COOH (XI)

wherein R'' represents:
- an alkylene radical, straight or branched, having from 1 to 30, preferably from 2 to 20, carbon atoms; or
- an alkylene-cycloalkylene-alkylene radical, having from 6 to 50 carbon atoms, preferably from 12 to 36 carbon atoms; or
- a cycloalkylene radical having from 6 to 30 carbon atoms, an arylene radical having from 6 to 30 carbon atoms; or wherein the alkylene, cycloalkylene and arylene radicals are:
- optionally substituted by at least one substituent selected from the group constituted of: alkyl, aryl and cycloalkyl; and/or
- optionally interrupted with at least one heteroatom chosen from the group consisting in: O, N and S.

According to an embodiment, R'' represents an alkylene-cycloalkylene-alkylene radical, having from 6 to 50 carbon atoms, preferably from 12 to 36 carbon atoms, and more preferably having 36 carbon atoms, the cycloalkylene radical being optionally substituted by two alkyl groups.

In particular, R'' represents the following radical:

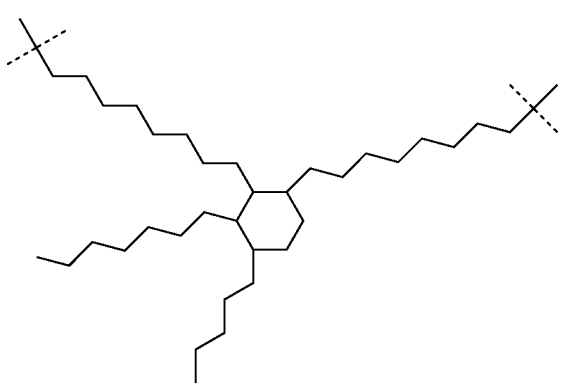

According to an embodiment, the diacid of formula (XI) is the Pripol® 1009 having the following formula:

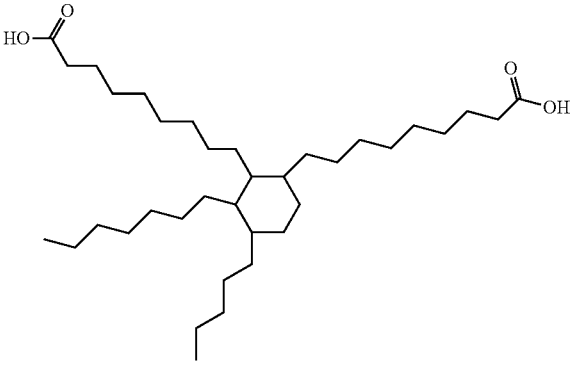 [SMILES: CCCCCCCC1C(CCCCC)CCC(CCCCCCCCC(=O)O)C1CCCCCCCCC(=O)O]

According to the invention, the polymer susceptible to be obtained by polymerization of the compound of formula (I) and a diacid derivative, in particular a diacid, as defined above, may have the following formula (IX) or (X):

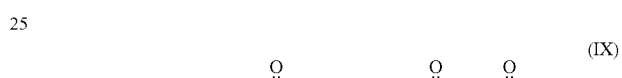

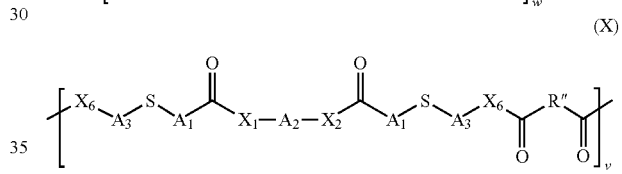

wherein:
$A_1, A_2, A_3, X_1$ and $X_2$ are as defined above in formula (I);
$X_7$ represents —O— or —NH—;
$X_6$ represents —O— or —NH—;
v and w, independently of each other, represent a integer comprised from 1 to 50000, preferably from 1 to 5000, and more preferably from 1 to 50;
R'' is as defined above in formula (XI).

According to an embodiment, in formula (IX) or (X), $A_1$ represents a straight divalent alkylene radical, having from 3 to 20, preferably from 3 to 12 carbon atoms, and optionally comprising at least one double bond, and/or optionally substituted by at least one hydroxyl or amine group.

According to an embodiment, in formula (IX) or (X), $A_1$ represents a straight divalent alkylene radical, having from 3 to 20, preferably from 3 to 12 carbon atoms.

In particular, $A_1$ represents a straight divalent alkylene radical having 10 carbon atoms.

According to an embodiment, in formula (X), v represents an integer comprised from 2 to 50000, preferably from 2 to 5000, and more preferably from 2 to 50.

According to an embodiment, in formula (IX), w represents an integer comprised from 2 to 50000, preferably from 2 to 5000, and more preferably from 2 to 50.

According to an embodiment, in formula (IX) or (X), $X_1$ represents —NH—.

According to an embodiment, in formula (IX) or (X), $X_2$ represents —NH—.

According to an embodiment, in formula (X), $X_6$ represents —O—.

According to an embodiment, in formula (IX), $X_7$ represents —O—.

According to an embodiment, in formula (IX) or (X), $A_3$ represents a divalent alkylene radical, straight or branched, having from 2 to 5 carbon atoms.

In particular, in formula (IX) or (X), $A_3$ represents a divalent alkylene radical, straight or branched, having 2 carbon atoms.

According to an embodiment, in formula (IX) or (X), $A_2$ represents a divalent alkylene radical, straight or branched, having from 3 to 8, preferably from 3 to 5 carbon atoms, and optionally comprising at least one double bond, and/or optionally substituted by at least one hydroxyl or amine group. In particular, $A_2$ represents a divalent alkylene radical, straight or branched, having 3 or 4 carbon atoms. Preferably, $A_2$ represents a straight divalent alkylene radical having 4 carbon atoms.

According to an embodiment, in formula (IX) or (X), R" represents:
- an alkylene radical, straight or branched, having from 1 to 30, preferably from 2 to 20, carbon atoms; or
- an alkylene-cycloalkylene-alkylene radical, having from 6 to 50 carbon atoms, preferably from 12 to 36 carbon atoms; or
- a cycloalkylene radical having from 6 to 30 carbon atoms,
- an arylene radical having from 6 to 30 carbon atoms; or wherein the alkylene, cycloalkylene and arylene radicals are:
- optionally substituted by at least one substituent selected from the group constituted of: alkyl, aryl and cycloalkyl; and/or
- optionally interrupted with at least one heteroatom chosen from the group consisting in: O, N and S.

In particular, in formula (IX) or (X), R" represents an alkylene-cycloalkylene-alkylene radical, having from 6 to 50 carbon atoms, preferably from 12 to 36 carbon atoms, and more preferably having 36 carbon atoms, the cycloalkylene radical being optionally substituted by two alkyl groups.

In particular, R" represents the following radical:

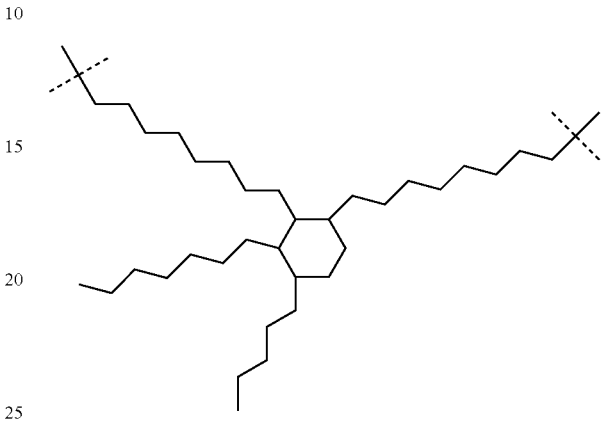

Preferably, the polymer susceptible to be obtained by polymerization of a compound of formula (I) and of a diacid derivative as defined above (in particular a diacid), has the following formula (X-1):

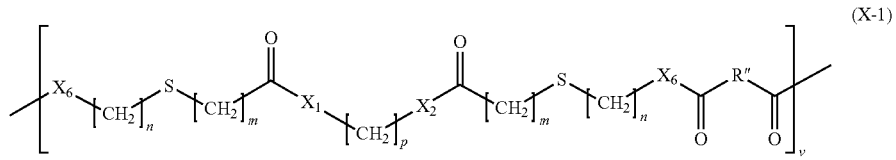

(X-1)

wherein:
n, m and p are as defined above in formula (I-2-1);
$X_1$ and $X_2$ are as defined above in formula (I);
$X_6$, R" and v are as defined above in formula (X).

The compound of formula (X-1) corresponds to a compound of formula (X) wherein:
$A_3$ represents —$(CH_2)_n$—;
$A_1$ represents —$(CH_2)_m$—; and
$A_2$ represents —$(CH_2)_p$—.

Preferably, the polymer of formula (X-1-1) is a polymer of formula (X-1-1):

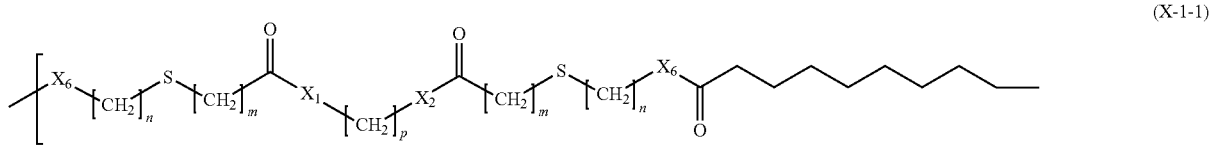

(X-1-1)

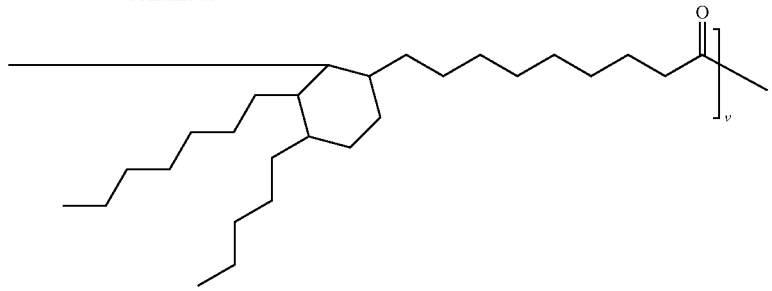

In particular, among the polymers of formula (X-1-1), mention is made of the following:

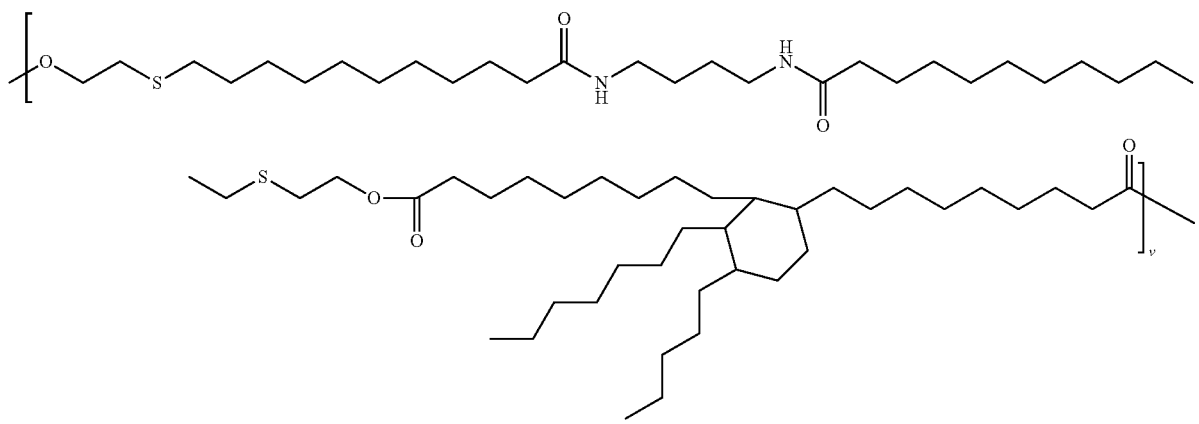

According to an embodiment, the compounds of formula (IX) or (X) may possess different terminal moieties, depending on the stoechiometry of the reactants used for the preparation of said polymers.

For example, if a diacid derivative, such as a diester or a dianhydride of formula (XI) is used in large excess compared to the compound of formula (I), then the polymer has diester or dianhydride functions as terminal moieties.

For example, if a diacid in particular a diacid of formula (XI) is used in large excess compared to the compound of formula (I), then the polymer has acid functions as terminal moieties.

For example, if a compound of formula (I) is used in large excess compared to diacid in particular a diacid of formula (XI), then the polymer has —OH or —NH$_2$ as terminal moieties.

For example, the polymer may also contain different terminal moieties on the polymer, namely an acid function at one end of the polymer and a —OH or —NH$_2$ at the other end of the polymer.

The present invention also concerns the use of a compound having the following formula (I):

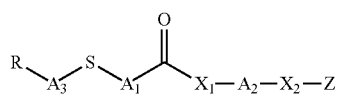

(I)

wherein:
R represents —OH or —NH$_2$;
$A_1$ represents a divalent alkylene radical, straight or branched, having from 2 to 20, preferably from 2 to 12 carbon atoms, and optionally comprising at least one double bond, and/or optionally substituted by at least one hydroxyl or amine group;
$A_2$ represents a divalent alkylene radical, straight or branched, having from 1 to 20, preferably from 1 to 10 carbon atoms, and optionally comprising at least one double bond, and/or optionally substituted by at least one hydroxyl or amine group;
$X_1$ and $X_2$ represent, independently of each other, —NH— or —O—;
$A_3$ represents a divalent alkylene radical, straight or branched, having from 1 to 10, preferably from 1 to 5 carbon atoms, and optionally comprising at least one double bond, and/or optionally substituted by at least one hydroxyl or amine group;
Z represents a hydrogen or a group of formula (A'):

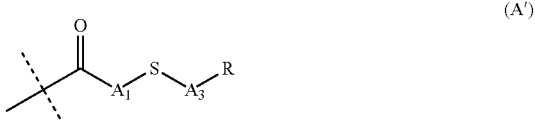

(A')

for the preparation of additives in a polyester matrix, poly (vinyl chloride) matrix, polyurethane matrix, polyimide matrix, poly(alkyl acrylate) matrix, poly(alkyl methacrylate) matrix, polystyrene matrix or polyolefin matrix, and notably in a poly(lactic acid) matrix.

According to an embodiment, the present invention concerns the use as defined above of a compound having the following formula (I):

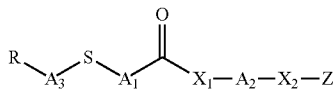
(I)

wherein:
R represents —OH or —NH$_2$;
A$_1$ represents a divalent alkylene radical, straight or branched, having from 3 to 20, preferably from 3 to 12 carbon atoms, and optionally comprising at least one double bond, and/or optionally substituted by at least one hydroxyl or amine group;
A$_2$ represents a divalent alkylene radical, straight or branched, having from 3 to 20, preferably from 3 to 10 carbon atoms, and optionally comprising at least one double bond, and/or optionally substituted by at least one hydroxyl or amine group;
X$_1$ and X$_2$ represent, independently of each other, —NH— or —O—;
A$_3$ represents a divalent alkylene radical, straight or branched, having from 1 to 10, preferably from 1 to 5 carbon atoms, and optionally comprising at least one double bond, and/or optionally substituted by at least one hydroxyl or amine group;
Z represents a hydrogen or a group of formula (A'):

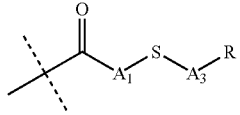
(A')

wherein when X$_1$ and X$_2$ represent —O—, then R represents —NH$_2$.

According to an embodiment, in formula (I), A$_1$ represents a straight divalent alkylene radical, having from 3 to 20, preferably from 3 to 12 carbon atoms, and optionally comprising at least one double bond, and/or optionally substituted by at least one hydroxyl or amine group.

According to an embodiment, in formula (I), A$_1$ represents a straight divalent alkylene radical, having from 3 to 20, preferably from 3 to 12 carbon atoms.

According to an embodiment, in formula (I), when R represents OH, then A$_1$ is a straight divalent alkylene radical having from 3 to 20, preferably from 3 to 12 carbon atoms and optionally comprising at least one double bond, and/or optionally substituted by at least one hydroxyl or amine group.

According to an embodiment, the present invention concerns the use as mentioned above of a compound having the following formula (I):

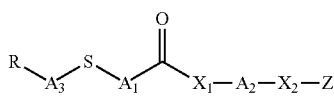
(I)

wherein:
R represents —OH or —NH$_2$,
A$_1$ represents a straight divalent alkylene radical having from 3 to 20, preferably from 3 to 12 carbon atoms;
A$_2$ represents a divalent alkylene radical, straight or branched, having from 3 to 20, preferably from 3 to 10 carbon atoms;
X$_1$ and X$_2$ represent, independently of each other, —NH— or —O—;
A$_3$ represents a divalent alkylene radical, straight or branched, having from 1 to 10, preferably from 1 to 5 carbon atoms;
Z represents a hydrogen or a group of formula (A'):

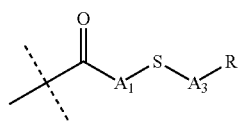
(A')

wherein when X$_1$ and X$_2$ represent —O—, then R represents —NH$_2$.

According to another embodiment, the present invention concerns the use as mentioned above of a compound having the following formula (I):

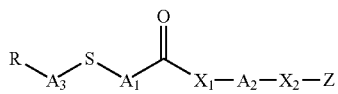
(I)

wherein:
R represents —OH or —NH$_2$,
A$_1$ represents a straight divalent alkylene radical having from 3 to 20, preferably from 3 to 12 carbon atoms;
A$_2$ represents a divalent alkylene radical, straight or branched, having from 3 to 20, preferably from 3 to 10 carbon atoms;
X$_1$ and X$_2$ represent, independently of each other, —NH— or —O—;
A$_3$ represents a divalent alkylene radical, straight or branched, having from 1 to 10, preferably from 1 to 5 carbon atoms;
Z represents a hydrogen or a group of formula (A'):

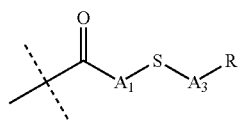
(A')

wherein when X$_1$ and X$_2$ represent —O—, then R represents —NH$_2$.

In a preferred embodiment, the present invention relates to the use as defined above of a compound of formula (I-1) as defined above, wherein the compound of formula (I-1) is preferably chosen from the group consisting of:

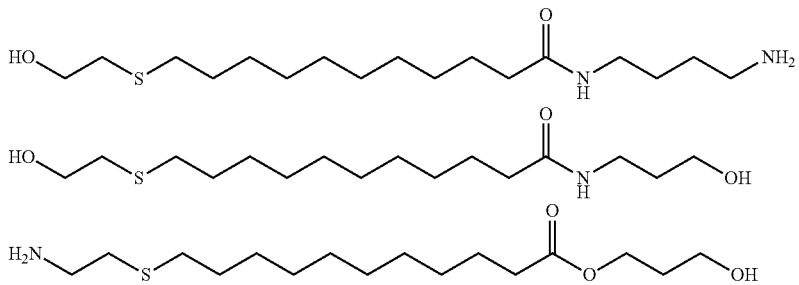

According to an embodiment, the present invention relates to the use as defined above of a compound of formula (I-2) as defined above, and more particularly of a compound of formula (I-2-1) as defined above which is preferably chosen in the group consisting of:

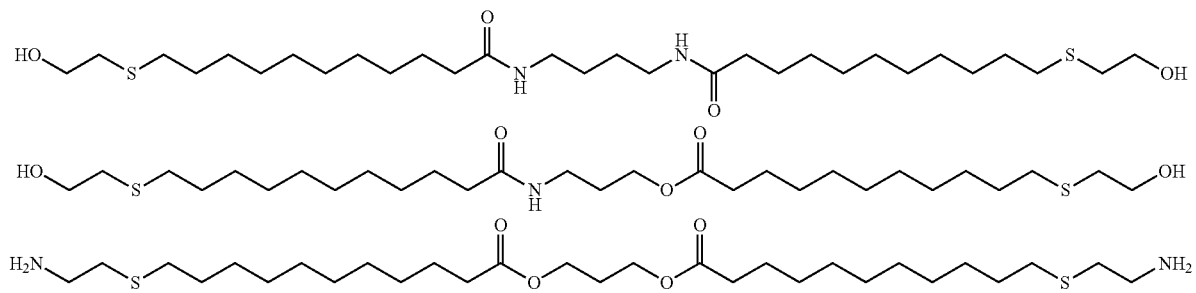

In a preferred embodiment, the present invention relates to the use as defined above of the following compound:

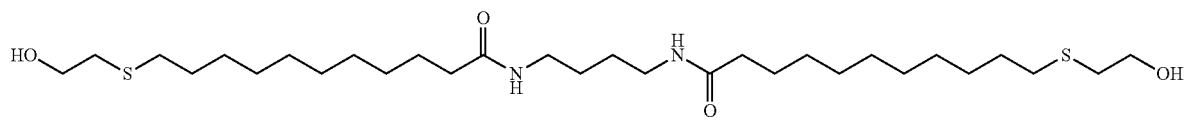 [SMILES: O=C(CCCCCCCCCCSCCO)NCCCCNC(=O)CCCCCCCCCCSCCO]

As used herein, the compounds of formula (I) designate precursors for the preparation of additives according to the invention. For example, compounds of formula (I) allow synthesizing compounds of formulae (VII), (VIII), (IX) and (X) which are polymers.

As used herein, the term "additives" encompasses the compounds of formulae (VII), (VIII), (IX) and (X) which are added in a polymer matrix, and more particularly compounds of formula (X).

As used herein, it is meant by "polymer matrix", a majority dispersing and continuous phase of a polymer comprising a dispersed and discontinuous phase of one or several additives according to the invention, and optionally at least one soft polymer. For example, the poly(lactic acid) is a polymer matrix.

According to the invention, a polymer matrix may be selected in the group consisting of: a polyester matrix, poly(vinyl chloride) matrix, polyurethane matrix, polyamide matrix, poly(alkyl acrylate) matrix, poly(alkyl methacrylate) matrix, polystyrene matrix and polyolefin matrix. Preferably, the polymer matrix is a poly(lactic acid) matrix, and more preferably a poly(L-lactic acid) matrix.

According to an embodiment, the present invention relates to the use of compound of formula (I), and more particularly of formula (I-1) or (I-2), for the preparation of additives of formula (VII), (VIII), (IX) or (X), said additives being intended to be used in a polyester matrix, poly(vinyl chloride) matrix, polyurethane matrix, polyamide matrix, poly(alkyl acrylate) matrix, poly(alkyl methacrylate) matrix, polystyrene matrix and polyolefin matrix, for improving the toughness and/or for enhancing the crystalline ability of said matrix.

According to an embodiment, the present invention relates to the use of the compounds of formula (VII), (VIII), (IX) or (X) as additives in a polyester matrix, poly(vinyl chloride) matrix, polyurethane matrix, polyamide matrix, poly(alkyl acrylate) matrix, poly(alkyl methacrylate) matrix, polystyrene matrix and polyolefin matrix, for improving the toughness of said matrix, and/or for enhancing the crystalline ability of said matrix.

The present invention concerns in particular the use of the compounds of formula (X) as additives in a polyester matrix, poly(vinyl chloride) matrix, polyurethane matrix, polyamide matrix, poly(alkyl acrylate) matrix, poly(alkyl methacrylate) matrix, polystyrene matrix and polyolefin matrix, for improving the toughness of said matrix, and/or for enhancing the crystalline ability of said matrix.

As used herein, the "improvement of the toughness of a polymer matrix" is considered as the improvement of the mechanical properties (higher elongation at break, decrease of the brittle behaviour of the material), especially observed by dispersion of an additive in the polymer matrix allowing said improvement of the toughness.

As used herein, the "enhancement of the crystalline ability of a polymer matrix" corresponds to an improvement for crystallizing and/or improvement for the phase segregation of said matrix according to the thermo dynamical laws, leading in particular to the obtaining of cylinder, lamellate phases . . . . Such enhancement is particularly due to the role of nucleating agent of the additive for the matrix. By nucleating agent is meant an additive that favors the formation of nuclei and thus improves the crystallization kinetics.

According to an embodiment, the present invention relates to the use of the compounds of formula (VII), (VIII), (IX) or (X) as additives in a polyester matrix, poly(vinyl chloride) matrix, polyurethane matrix, polyamide matrix, poly(alkyl acrylate) matrix, poly(alkyl methacrylate) matrix, polystyrene matrix and polyolefin matrix, for improving the toughness of said matrix, and/or as nucleating agent of the polymer matrix.

According to an embodiment, the polymer matrix is a polyester matrix, and in particular a poly(lactic acid) matrix.

According to an embodiment, the additives are selected in the group consisting of the compounds of formula (VII), (VIII), (IX) or (X):

$A_3$ represents a divalent alkylene radical, straight or branched, having from 1 to 10, preferably from 1 to 5 carbon atoms, and optionally comprising at least one double bond, and/or optionally substituted by at least one hydroxyl or amine group;

$X_7$ represents —O— or —NH—;

$X_6$ represents —O— or —NH—;

$X_4$ represents —NH— or —O—;

n is comprised from 1 to 10, preferably from 1 to 5;

m is comprised from 2 to 20, preferably from 5 to 15;

p is comprised from 1 to 20, preferably from 1 to 10; and $X_5$ represents —CH$_2$— or —CH$_2$S—;

$A_5$ represents an alkylene radical, straight or branched, having from 1 to 12 carbon atoms, said alkylene radical being eventually substituted by an alkyl group having from 1 to 10 carbon atoms, and said alkylene radical eventually comprising a double bond;

v and w, independently of each other, represent a integer comprised from 1 to 50000, preferably from 1 to 5000, and more preferably from 1 to 50;

t represents a integer comprised from 1 to 50000, preferably from 1 to 5000, and more preferably from 1 to 50;

u represents a integer comprised from 1 to 50000, preferably from 1 to 5000, and more preferably from 1 to 50;

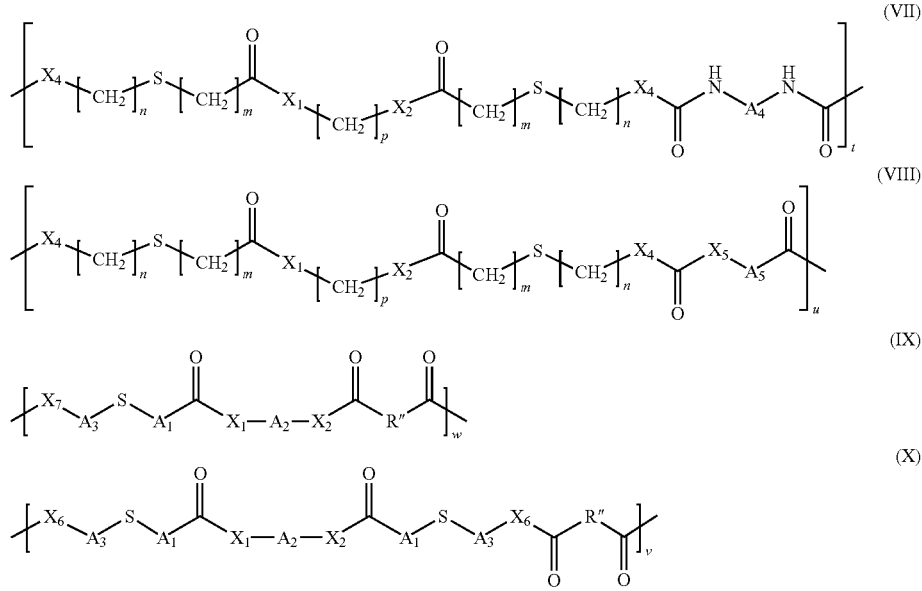

wherein:

$A_1$ represents a divalent alkylene radical, straight or branched, having from 2 to 20, preferably from 2 to 12 carbon atoms, and optionally comprising at least one double bond, and/or optionally substituted by at least one hydroxyl or amine group;

$A_2$ represents a divalent alkylene radical, straight or branched, having from 1 to 20, preferably from 1 to 10 carbon atoms, and optionally comprising at least one double bond, and/or optionally substituted by at least one hydroxyl or amine group;

$X_1$ and $X_2$ represent, independently of each other, —NH— or —O—;

R″ represents:
an alkylene radical, straight or branched, having from 1 to 30, preferably from 2 to 20, carbon atoms; or
an alkylene-cycloalkylene radical, having from 6 to 50 carbon atoms, preferably from 12 to 36 carbon atoms; or
an arylene radical having from 6 to 30 carbon atoms; or
a polymer;

wherein the alkylene, cycloalkylene and arylene radicals are:
optionally substituted by at least one substituent selected from the group constituted of: alkyl, aryl and cycloalkyl, and/or optionally interrupted with at least one heteroatom chosen from the group consisting in: O, N and S.

Preferred additives according to the invention are those of formula (X) as defined above, wherein:

$X_6$ represents —O—;
$X_1$ and $X_2$ represent —NH—;
v is as defined above;
$A_2$ represents —$(CH_2)_4$—;
$A_3$ represents —$(CH_2)_2$—;
$A_1$ represents —$(CH_2)_{10}$—;
R" represents an alkylene-cycloalkylene-alkylene radical, having from 6 to 50 carbon atoms, preferably from 12 to 36 carbon atoms, and more preferably having 36 carbon atoms, the cycloalkylene radical being optionally substituted by two alkyl groups, and preferably R" represents:

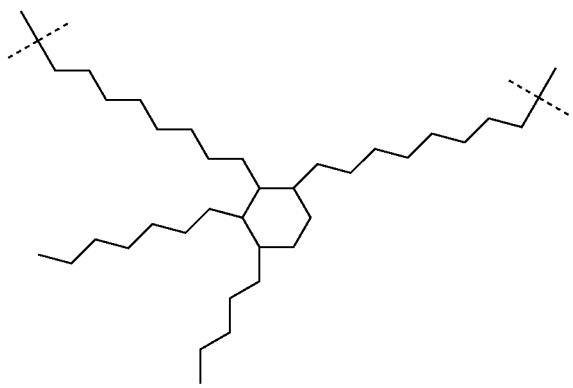

Preferred additives according to the invention, are those of formula (X-1), and more particularly of formula (X-1-1) as defined above.

The present invention also concerns a composition comprising:
- a matrix chosen from the group consisting of: a polyester matrix, a poly(vinyl chloride) matrix, a polyurethane matrix, a polyamide matrix, a poly(alkyl acrylate) matrix, a poly(alkyl methacrylate) matrix, a polystyrene matrix and a polyolefin matrix, and notably a poly(lactic acid) matrix; and
- at least one compound of formula (VII), (VIII), (IX) or (X), or their mixtures; and
- optionally another polymer notably selected from the group consisting of: poly(butadiene), poly(isoprene), poly(ε-caprolactone), poly(ricinoleic acid) and poly(tetrahydrofurane), and mixtures thereof.

According to an embodiment, the present invention concerns a composition comprising:
- a matrix chosen from the group consisting of: a polyester matrix, a poly(vinyl chloride) matrix, a polyurethane matrix, a polyamide matrix, a poly(alkyl acrylate) matrix, a poly(alkyl methacrylate) matrix, a polystyrene matrix and a polyolefin matrix, and notably a poly(lactic acid) matrix; and
- at least one compound of formula (VII), (VIII), (IX) or (X), or their mixtures; and
- another polymer notably selected from the group consisting of: poly(butadiene), poly(isoprene), poly(ε-caprolactone), poly(ricinoleic acid) and poly(tetrahydrofurane), and mixtures thereof.

According to an embodiment, the present invention concerns compositions comprising from 0% to 40% by weight, preferably from 5% to 20% by weight, of a polymer chosen from poly(butadiene), poly(isoprene), poly(ε-caprolactone), and poly(tetrahydrofurane), in a polymer matrix chosen in the group consisting of; a polyester matrix, a poly(vinyl chloride) matrix, a polyurethane matrix, a polyamide matrix, a poly(alkyl acrylate) matrix, a poly(alkyl methacrylate) matrix, a polystyrene matrix and a polyolefin matrix, compared to the total weight of the composition, as well as at least one compound of formula (VII), (VIII), (IX) or (X), or their mixtures.

According to an embodiment, the present invention concerns the above-mentioned compositions comprising from 60% to 95% by weight, preferably from 80% to 95% by weight of a polymer matrix chosen in the group consisting of; a polyester matrix, a poly(vinyl chloride) matrix, a polyurethane matrix, a polyamide matrix, a poly(alkyl acrylate) matrix, a poly(alkyl methacrylate) matrix, a polystyrene matrix and a polyolefin matrix.

According to an embodiment, the present invention concerns the above-mentioned compositions comprising from 2% to 40% by weight, preferably from 5% to 20% by weight of an additive of formula (VII), (VIII), (IX) or (X), compared to the total weight of the composition.

In particular, the present invention concerns the above-mentioned compositions comprising 5% by weight of an additive of formula (VII), (VIII), (IX) or (X), compared to the total weight of the composition.

In particular, the present invention concerns the above-mentioned compositions comprising 10% by weight of an additive of formula (VII), (VIII), (IX) or (X), compared to the total weight of the composition.

In particular, the present invention concerns compositions the above-mentioned comprising 15% by weight of an additive of formula (VII), (VIII), (IX) or (X), compared to the total weight of the composition.

In particular, the present invention concerns the above-mentioned compositions comprising 20% by weight of an additive of formula (VII), (VIII), (IX) or (X), compared to the total weight of the composition.

According to an embodiment, the invention concerns the above-mentioned compositions comprising 5% by weight of an additive of formula (X), and more particularly of formula (X-1-1) and 95% by weight of a polymer matrix chosen in the group consisting of; a polyester matrix, a poly(vinyl chloride) matrix, a polyurethane matrix, a polyamide matrix, a poly(alkyl acrylate) matrix, a poly(alkyl methacrylate) matrix, a polystyrene matrix and a polyolefin matrix.

According to an embodiment, the invention concerns the above-mentioned compositions comprising 10% by weight of an additive of formula (X) and more particularly of formula (X-1-1), and 90% by weight of a polymer matrix chosen in the group consisting of; a polyester matrix, a poly(vinyl chloride) matrix, a polyurethane matrix, a polyamide matrix, a poly(alkyl acrylate) matrix, a poly(alkyl methacrylate) matrix, a polystyrene matrix and a polyolefin matrix.

According to an embodiment, the invention concerns the above-mentioned compositions comprising 15% by weight of an additive of formula (X) and more particularly of formula (X-1-1), and 85% by weight of polymer matrix chosen in the group consisting of; a polyester matrix, a poly(vinyl chloride) matrix, a polyurethane matrix, a polyamide matrix, a poly(alkyl acrylate) matrix, a poly(alkyl methacrylate) matrix, a polystyrene matrix and a polyolefin matrix.

According to an embodiment, the invention concerns the above-mentioned compositions comprising 20% by weight of an additive of formula (X) and more particularly of formula (X-1-1), and 80% by weight of a polymer matrix chosen in the group consisting of; a polyester matrix, a poly(vinyl chloride) matrix, a polyurethane matrix, a polyamide matrix, a poly(alkyl acrylate) matrix, a poly(alkyl methacrylate) matrix, a polystyrene matrix and a polyolefin matrix.

In particular, when the additives of formula (IX) or (X) result from the use of Pripol®, namely a compound of formula:

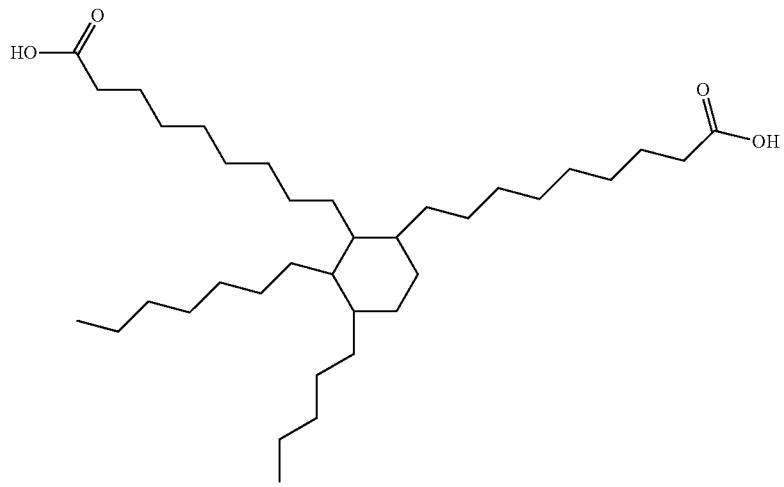 [SMILES: CCCCCCCC1C(CCCCC)CCC(CCCCCCCCC(=O)O)C1CCCCCCCCC(=O)O]

then, the composition as defined above does not contain another polymer notably selected from the group consisting of: poly(butadiene), poly(isoprene), poly(ε-caprolactone), and poly(tetrahydrofurane). Indeed, it was advantageously shown that incorporation of Pripol® in the polymers of formula (IX) or (X), leads to plasticizer and nucleating polymers, which provides softening of the polymer matrix. Therefore the use of other soft polymers may not be necessary.

According to an embodiment, the present invention concerns a composition comprising a poly(lactic acid) matrix, and at least one compound of formula (VII), (VIII), (IX) or (X). In particular, the present invention concerns a composition comprising a poly(lactic acid) matrix, and at least one compound of formula (X), and preferably a compound of formula (X-1-1).

The use of compounds of formula (VII), (VIII), (IX) or (X), or their mixtures, advantageously allows to improve the toughness of a polymer matrix, such as polyester, poly(vinyl chloride), polyurethane, polyamide, poly(alkyl acrylate), poly(alkyl methacrylate), polystyrene and polyolefin matrix, without affecting the other mechanical properties of the polymer of said matrix. More particularly, the use of compounds of formula (VII), (VIII), (IX) or (X) according to the invention, advantageously allows to increase the elongation at break of the polymer matrix, which allows overcoming the brittleness of the polymer matrix. Therefore, such use allows to provide with a more flexible polymer matrix, and/or to improve its deformation at high or cold temperature.

Besides, the use of at least one compound of formula (VII), (VIII), (IX) or (X), or their mixtures, in a polymer matrix, optionally comprising a soft polymer, advantageously allows enhancing the crystalline ability of the matrix polymer. Said compounds of formula (VII), (VIII), (IX) or (X) advantageously act as nucleating agents which allows the crystallization of the polymer of polymer matrix.

In conclusion, the use of at least one compound of formula (VII), (VIII), (IX) or (X) in a poly(lactic acid) matrix, advantageously allows improving the toughness of the matrix and/or enhancing the crystalline ability of said matrix.

EXAMPLES

Suppliers

Undecenoate methyl ester (>98.0%): TCI
2-mercaptoethanol (98%): TCI
Cysteamine hydrochloride (>95%): TCI
1,4-diaminobutane (99%): Jassen Chemica
Trifluoroacetic anhydride (TFAA): Jassen Chemica
1,5,7-triazabicyclo[4.4.0]dec-5-ene (TBD, 98%): Sigma Aldrich
Isophorone diisocyanate (IPDI, 98%): Sigma Aldrich
Azobisisobutyronitrile (AIBN, 98%): Sigma Aldrich
2,2-dimethoxy-2-phenylacetophenone (DMPA, 99%): Sigma Aldrich
Dibutyl tin dilaurate (DBTDL, 95%): Alfa Aesar
N-methyl-2-pyrrolidinone (NMP, synthesis grade): Scharlau
Methanol (grade pur): Xilab
Ethanol (grade pur): Xilab
Dioxane (reagent grade): Scharlau
Tetrahydrofuran (THF, GC grade): Sigma Aldrich
N,N-dimethylformamide (DMF, HPLC grade): Scharlau.
All the products and solvent were used as received.

Example 1

Preparation of Compound (3)

1) Transamidification Reaction

One equivalent of undecenoate methyl ester (1) with 0.5 equivalent of 1,4-diaminobutane were stirred under nitrogen flux at 120° C. during 4 hours then at 160° C. during 2 hours. An organic catalyst TBD was employed at 5% molar compared with the quantity of (1). At the end of the reaction, the reaction flask was cooled down at 90° C., and N-methyl-2-pyrrolidinone (NMP) was added to end up with a homogeneous phase. The required undecenoic diamide bis-unsaturated (2) was slowly precipitated reaching room temperature. A classical filtration with methanol was performed in order to remove the catalyst and the undesired reactants. The compound (2) was obtained with a yield of 83 wt % after recrystallization in NMP.

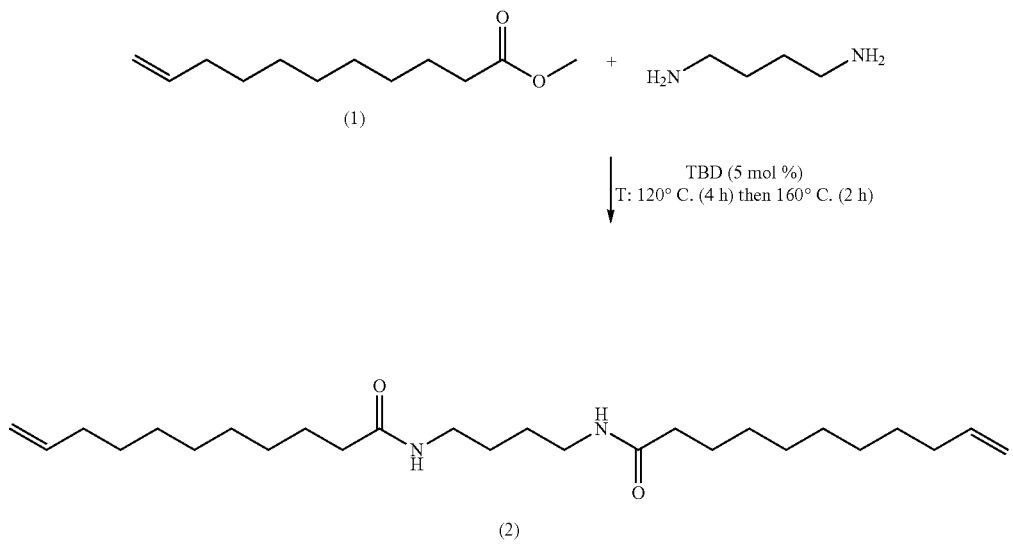

2) Thiolene Reaction

One equivalent of (2) was reacted with 12 equivalents per double bond of mercaptoethanol, with 5% molar of AIBN in relation to (2). NMP was added at 5 mL per grams of (2) to obtain a homogeneous mixture. The flask was immersed under static vacuum into a bath preheated at 80° C. The reaction was followed by H-NMR analysis and completed after 2 hours. The undecenoic diamide diol (3) was recovered by water washes with a yield of 92 wt % after purification. The melting temperature checked by DSC was at 150° C.

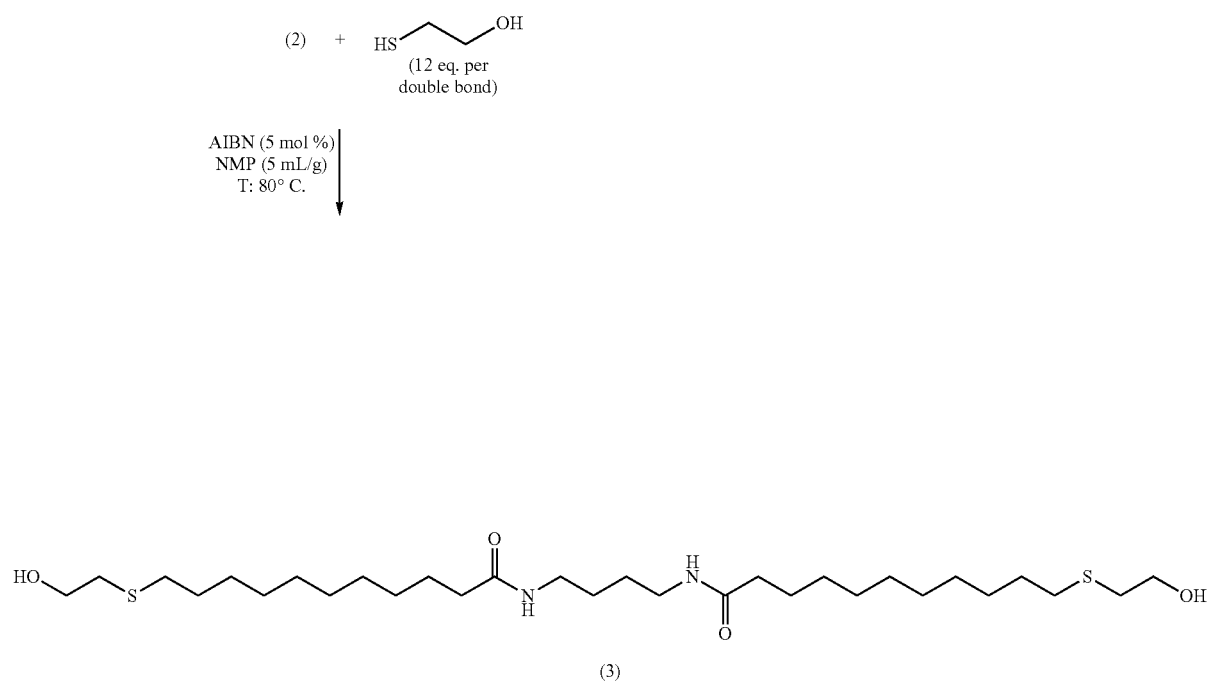

Example 2

Preparation of Compound (5)

1) Transamidification/Transesterification Reaction

One equivalent of undecenoate methyl ester (1) with 0.5 equivalent of 1,3-aminopropanol were stirred under nitrogen flux at 120° C. during 4 hours then at 160° C. during 2 hours. An organic catalyst TBD was employed at 5% molar compared with the quantity of (1). After the reaction, a column chromatography was performed with dichloromethane/methanol (95/5) and the desired compound (4) was recovered with a yield of 78 wt % after purification.

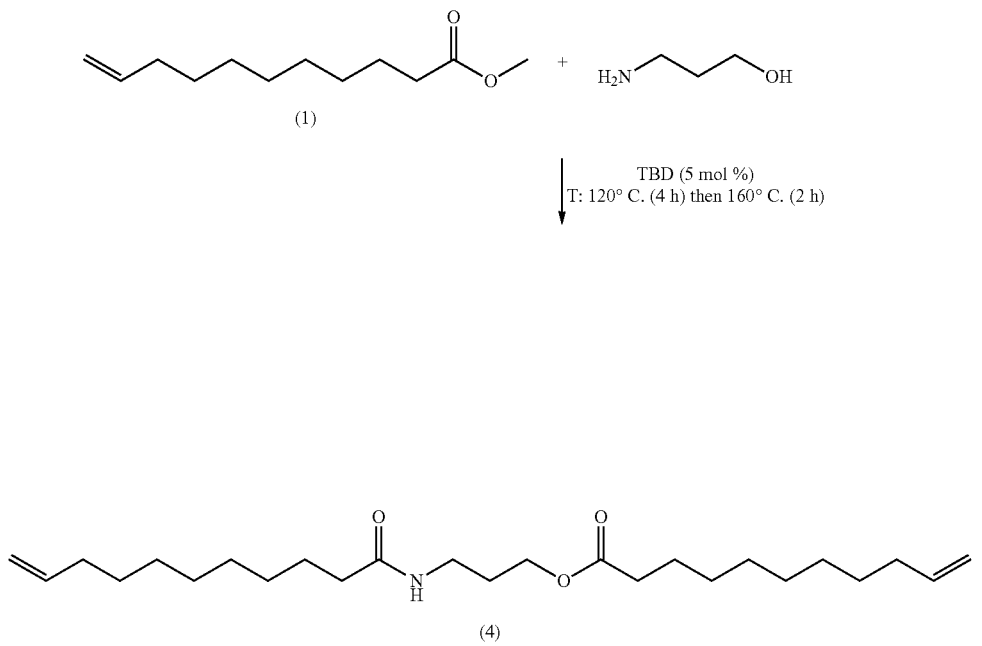

2) Thiolene Reaction

One equivalent of (4) was reacted with 6 equivalents per double bond of mercaptoethanol. Dichloromethane was added at 5 mL per grams of (4) to obtain a homogeneous mixture. The flask was put at room temperature under UV at 254 nm. After 6 hours, the conversion based on double bond protons by H-NMR was 98%. The reaction was completed after 3 days thanks to additional 12 equivalents per double bond of mercaptoethanol. The undecenoic esteramide diol (5) was recovered by several water washes with a yield of 70 wt % after purification.

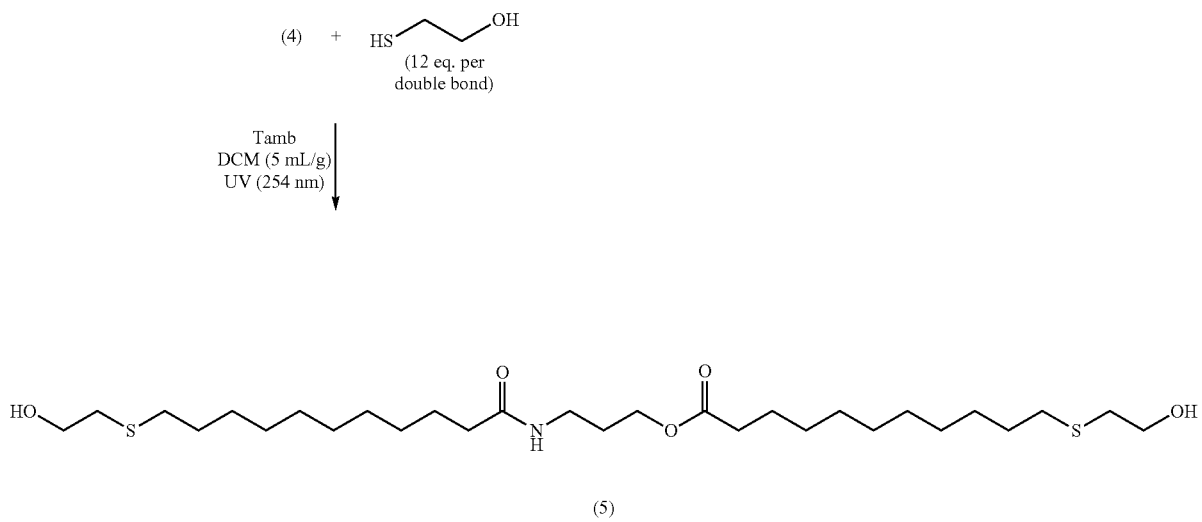

Example 3

Preparation of Compound (7)

1) Transesterification Reaction

One equivalent of undecenoate methyl ester (1) with 0.5 equivalent of 1,3-propanediol were stirred under nitrogen flux at 120° C. during 4 hours then at 160° C. during 2 hours. TBD was employed at 5% molar compared with the quantity of (1). At the end of the reaction, the mixture was dissolved in ethyl acetate and washed several times with water to remove catalyst and unreacted diol. Organic phase was then dried with sodium sulfate, filtrated and finally concentrated under reduce pressure in order to isolate the required undecenoate diester (6) bis-unsaturated. Compound (6) was isolated with a yield of 90 wt % after purifications.

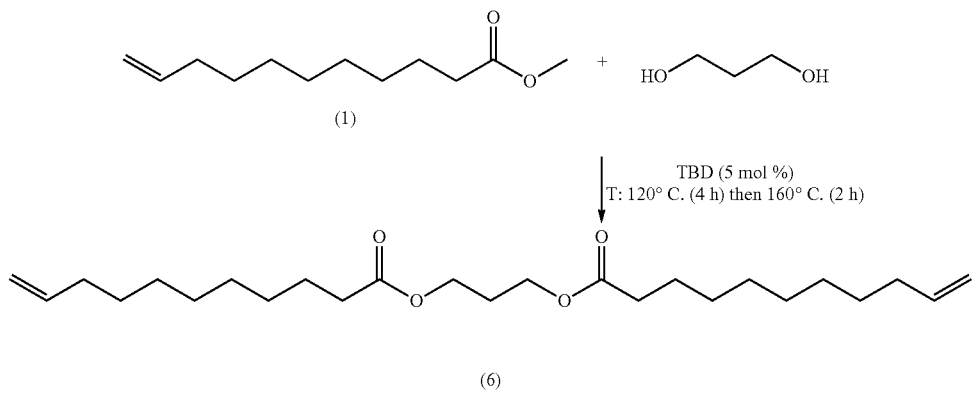

2) Thiolene Reaction

One equivalent of (6), 6 equivalents of cysteamine hydrochloride, 0.1 equivalent of DMPA and a mixture of Dioxane/Ethanol (70:30/v:v) with a volume of 6 mL per gram of diester were stirred at room temperature under UV for 6 hours. A wave length of 365 nm was used yielding 100% conversion of the double bond after 1 hour of reaction regarding to H-NMR analysis. After completion of the reaction, solvent was removed under reduced pressure and the reaction mixture was then stirred with a $Na_2CO_3$ saturated aqueous solution for few hours in order to remove unreacted cysteamine hydrochloride and to deprotonate amine functions. The obtained powder (7) was then filtrated and washed with acetone to remove water. Finally remaining acetone was removed under reduce pressure giving rise to a white powder exhibiting a melting point of 50° C. according to DSC analysis. The compound (7) was isolated with a yield of 70 wt % after purifications.

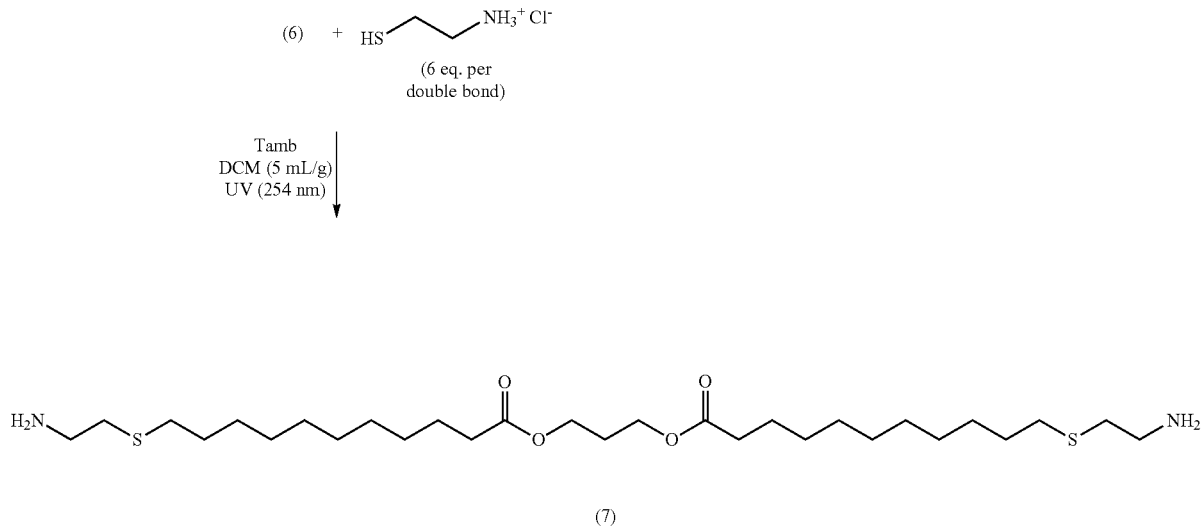

Example 4

Preparation of Compound (9)

1) Transamidification Reaction

One equivalent of undecenoate methyl ester (1) with 2 equivalents of 1,3-aminopropanol were stirred under nitrogen flux at 150° C. during 2 hours, then at 160° C. during 2 hours. No catalyst was used. A precipitation was done in water to wash the unreacted aminopropanol. The desired compound (8) was obtained with 5.2% of compound (4) (GPC analysis).

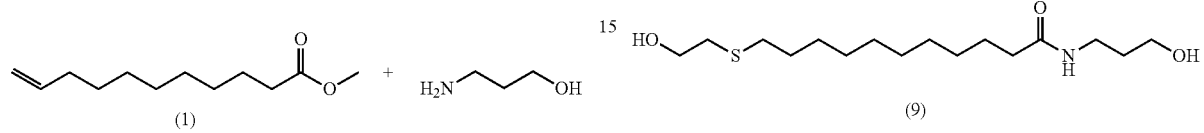

No catalyst
T: 150° C. (2 h) then 160° C. (2 h)

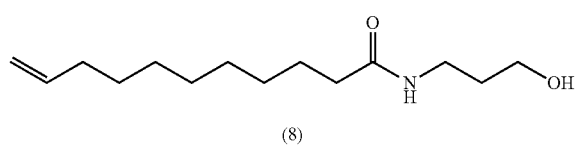

2) Thiolene Reaction

The thiolene reaction was carried out in the same experimental conditions as in example 2.

(8) + HS$\diagdown\diagdown$OH (12 eq. per double bond)

Tamb
DCM (5 mL/g)
UV (254 nm)

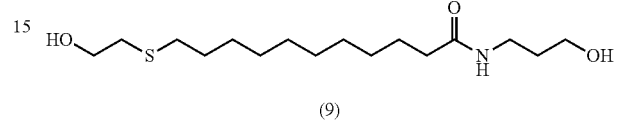

Example 5

Preparation of Polyurethane (10) from Compound (3)

Before using, compound (3) was dried under dynamic vacuum at 160° C. during 30 minutes then at 70° C. overnight. The polyurethane synthesis was performed at 80° C. or 90° C. with one equivalent of IPDI or MDI, DBTDL as catalyst and 10 mL/g of anhydrous DMF. After completion of the reaction followed by FTIR-ATR, the obtained polyurethane was precipitated in cold methanol, filtrated and dried.

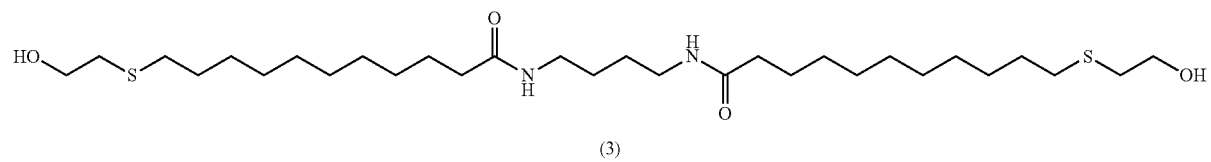

IPDI (1 eq.) | DBTDL (0.2 mol %)
DMF (10 mL/g)
T: 90° C.

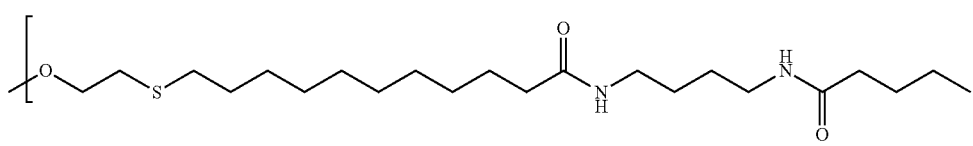

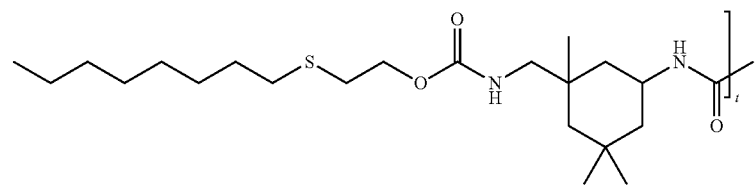

(10)

TABLE 1

Experimental results of polymerization

| Trial | Diisocyanate | Catalyst | T (° C.) | $M_n^{(a)}$ | $M_w^{(a)}$ | $Đ^{(a)}$ | $T_g^{(b1)}$ | $T_{m1}^{(b1)}$ | $T_{mc}^{(b2)}$ | $T_{m2,3,4}^{(b2)}$ | $T_{5\%}^{(c)}$ | $T_{max}^{(c)}$ |
|---|---|---|---|---|---|---|---|---|---|---|---|---|
| 1 | IPDI | 0.2% wt. DBTDL | 90 | 22 140 | 33 291 | 1.5 | 40 | 118 | — | — | 292 | 465 |
| 2$^{(d)}$ | IPDI | 0.1 wt % DBTDL | 80 | (ns) | (ns) | (ns) | 47 | 117 | — | — | 289 | 579 |
| 3$^{(d)}$ | MDI | — | 80 | (ns) | (ns) | (ns) | 47 | 155$^{(b2)}$ | 158 | 172, 178, 183 | 269 | 596 |

$^{(a)}$SEC in THF with TFAA solubilization procedure based on PS standards
$^{(b1)}$DSC 10° C./min
$^{(b2)}$Modulated DSC 2° C./min from 100° C. to 200° C. and after from 200° C. to 100° C.
$^{(c)}$TGA after 5% and full degradation 10° C./min to 700° C.
$^{(d)}$Reaction carried out in presence of LiCl
$^{(ns)}$The sample is not soluble The Tg (glass transition temperature) and Tm (melting temperature) around respectively 45° C. and 117° C. are obtained for the polyurethanes obtained from compound (3) and IPDI as diisocyanate. More elaborated thermo-mechanical properties with a melt crystallization are reached with the polyurethane from compound (3) and MDI as diisocyanate.

Example 6

Preparation of Polyurethane (11) from Compound (5)

Before using, the compound (5) was dried under dynamic vacuum at 120° C. during 30 minutes, then at 70° C. overnight. The polyurethane synthesis was performed at 80° C. with one equivalent of IPDI or MDI, DBTDL as catalyst and 10 mL/g of anhydrous DMF. After completion of the reaction followed by FTIR-ATR, the obtained polyurethane was precipitated in cold methanol, filtrated and dried.

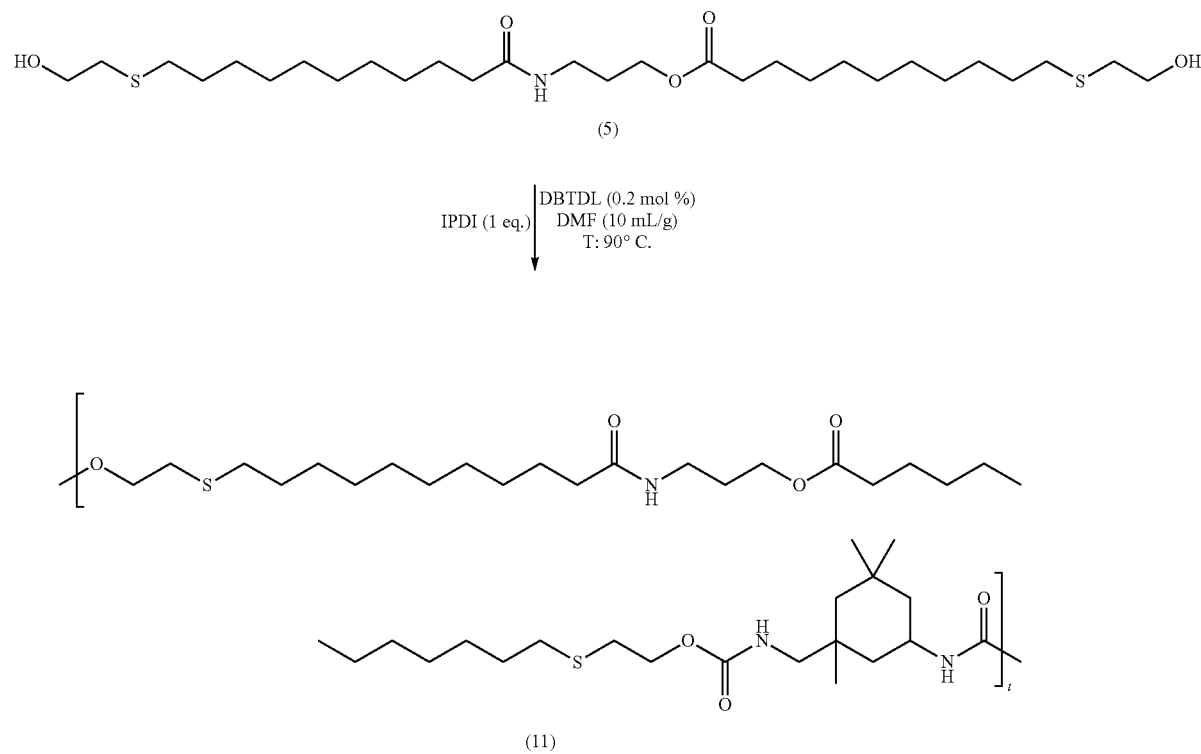

TABLE 2

Experimental results of polymerization

| Trial | Diisocyanate | Catalyst | T (° C.) | $M_n^{(a)}$ | $M_w^{(a)}$ | $D^{(a)}$ | $T_g^{(b)}$ | $T_{m1}^{(b)}$ | $T_{mc1,2}^{(b)}$ | $T_{m2}^{(b)}$ | $T_{5\%}^{(c)}$ | $T_{max}^{(c)}$ |
|---|---|---|---|---|---|---|---|---|---|---|---|---|
| 1 | IPDI | 0.1% wt. DBTDL | 80 | 40 000 | 50 000 | 1.4 | 17.0 | — | — | — | 302 | 475 |
| 2 | MDI | No | 80 | 60 000 | 95 000 | 1.6 | 22.5 | 107.8 | 79.6, 117.5 | 132.2 | 284 | 503 |

[a] SEC in DMF based on PS standards
[b] DSC 10° C./min
[c] TGA after 5% and full degradation 10° C./min to 600° C. (Tmc) Crystallization while heating

Example 7

Preparation of Polyester (12) from Compound (3)

a) Preparation of Diester A 20 g of methyl undecenoate were introduced in a 100 mL round-bottom flask in presence of 0.1 mol % of $2^{nd}$ generation Grubb's catalyst. The reaction mixture was stirred under low nitrogen flow for 3 days at 50° C. After completion of the reaction, the catalyst was deactivated with 1 mL of ethyl vinyl ether before applying dynamic vacuum for one hour. Desired product was purified by column chromatography using a mixture of cyclohexane/ethyl acetate (v/v: 95/5) as eluent.

b) Preparation of Diester B 10 g of methyl undecenoate were introduced in a 100 mL round-bottom flask with 3 equivalents of methyl thioglycolate. Reaction mixture was stirred under UV lamp at a wavelength of 254 nm for 6 hours. After completion of the reaction, excess methyl thioglycolate was removed by cryo-distillation at 80° C. under vacuum.

c) Preparation of Diester C 20 g of methyl oleate were introduced in a round-bottom flask with 3 equivalents of methyl thioglycolate and 0.05 equivalents of DMPA (2,2-dimethoxy-2-phenylacetophenone). Reaction mixture was then stirred for 2 hours under UV lamp at 365 nm. After completion of the reaction, excess methyl thioglycolate was removed by cryo-distillation.

d) Preparation of Polyester (12)

Polyester synthesis was performed at 180° C. for 4 hours under nitrogen flux following by 20 hours at 180° C. under dynamic vacuum to remove methanol released by transesterification. Reactions were performed in bulk using TBD (10 mol % per ester group) as a catalyst. 1 equivalent of diester was used for 1 equivalent of compound (3).

After completion of the reaction, polymers were dissolved in NMP by heating if necessary, precipitated in cold methanol and filtrated.

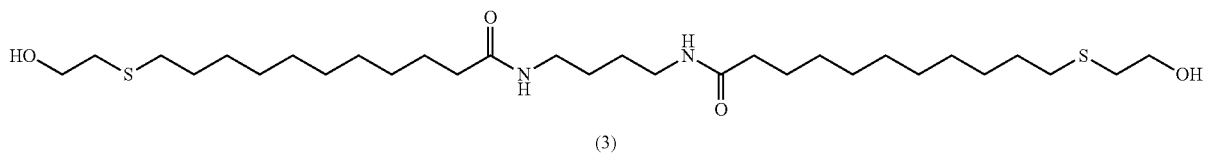

(3)

Diester A | TBD (10% mol per ester group)
T: 180° C. 4 h, N₂, then 180° C.,
20 h under dynamic vacuum

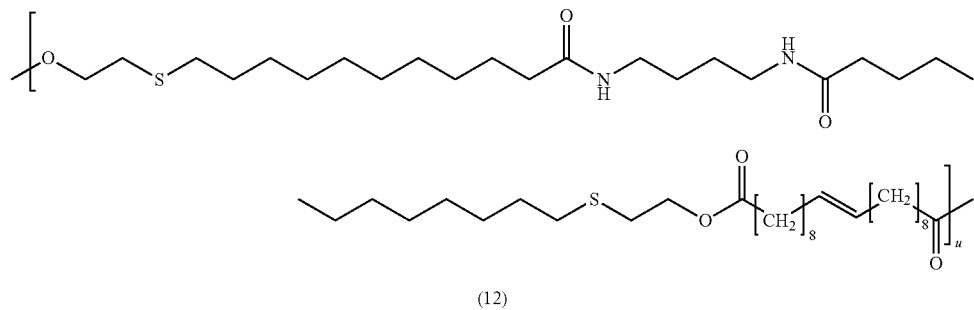

(12)

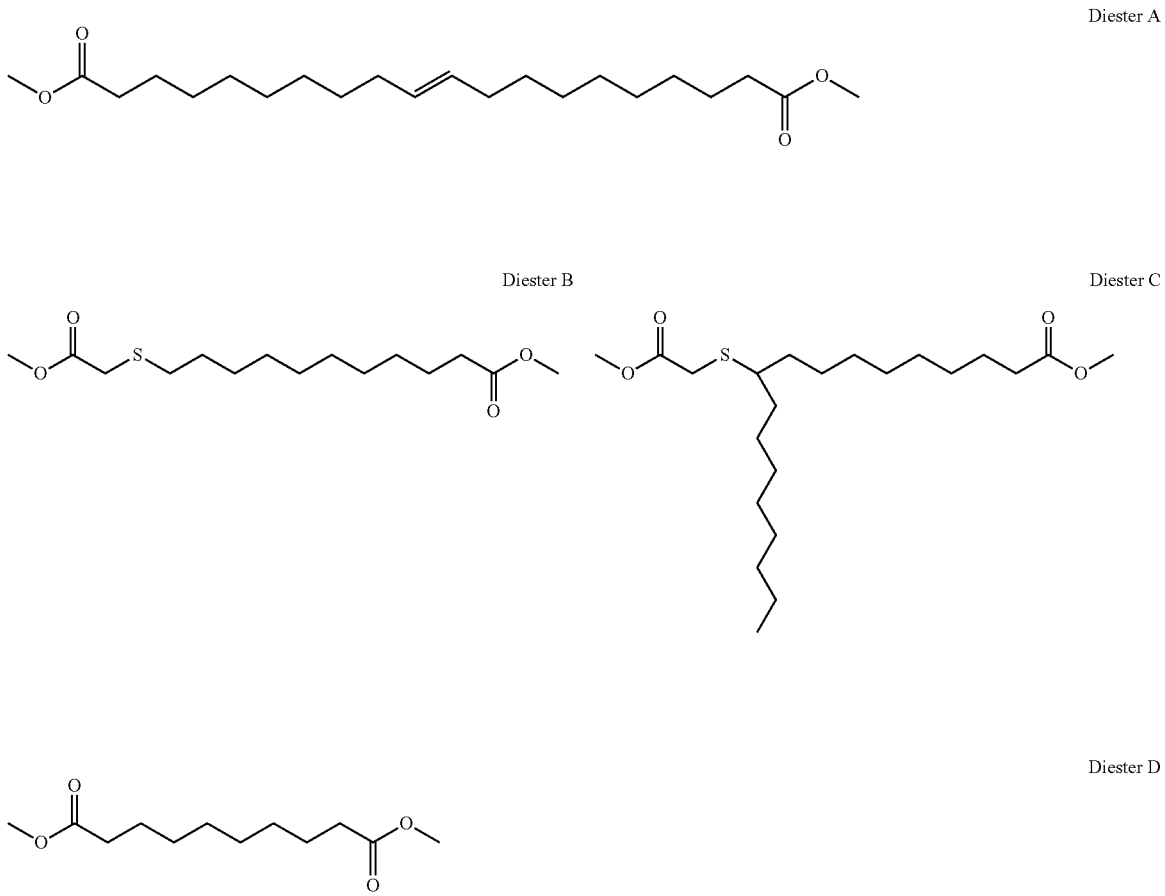

TABLE 3

Experimental results of polymerization

| Diester | $M_n$ (g/mol)[a] | $M_w$ (g/mol)[a] | $Đ$[a] | $T_g$ (° C.)[b] | $T_{m1}$ (° C.)[c] | $\Delta H_{m1}$ (J/g)[c] | $T_{m2}$ (° C.)[c] | $\Delta H_{m2}$ (J/g)[c] | $T_{5\%}$ (° C.)[d] |
|---|---|---|---|---|---|---|---|---|---|
| A | 19 092 | 29 028 | 1.5 | −10 | 122 | 64 | 128 | 7 | 345 |
| B | 9 472 | 12 641 | 1.3 | 2 | 120 | 31 | 126 | 16 | — |
| C | 10 930 | 17 610 | 1.6 | −13 | 118 | 64 | — | — | — |
| D | 6 522 | 9 524 | 1.5 | 5 | 129 | 8 | 138 | 33 | — |

[a]SEC in THF with TFAA solubilization procedure based on PS standards
[b]DMA 10° C./min
[c]DSC 10° C./min
[d]TGA after 5% degradation 10° C./min to 700° C.

It was observed on a DMA thermograph, that the difference of elastic modulus between the value before or after the glass transition highly depends on the nature of the polymer. This difference is higher for polymers made from the diesters B and C indicating that these materials exhibit a more important amorphous character.

It was observed on a tangent delta versus temperature plot, that Tg values for these polymers are ranging from −15° C. to 5° C. The intensity of tangent delta peak is much more important for polymers made from the diesters A, B and C than the one of polymer made from the diester D, indicating that the latter is more crystalline.

All the poly(ester-amide)s synthesized showed melting points ranging from 120° C. to 140° C. In some cases, two melting points are observed indicating that different crystalline phases are present in the polymer.

Example 8

Preparation of Polyester (13) from Compound (5)

The synthesis of polyester (13) was performed at 140° C. for 24 hours under dynamic vacuum to remove methanol released by transesterification. The reaction was performed in bulk using TBD (10 mol % per ester group) as catalyst. 1 equivalent of diester was used for 1 equivalent of compound (5). After completion of the reaction, the polymer was dissolved in dichloromethane, precipitated in cold methanol and filtrated.

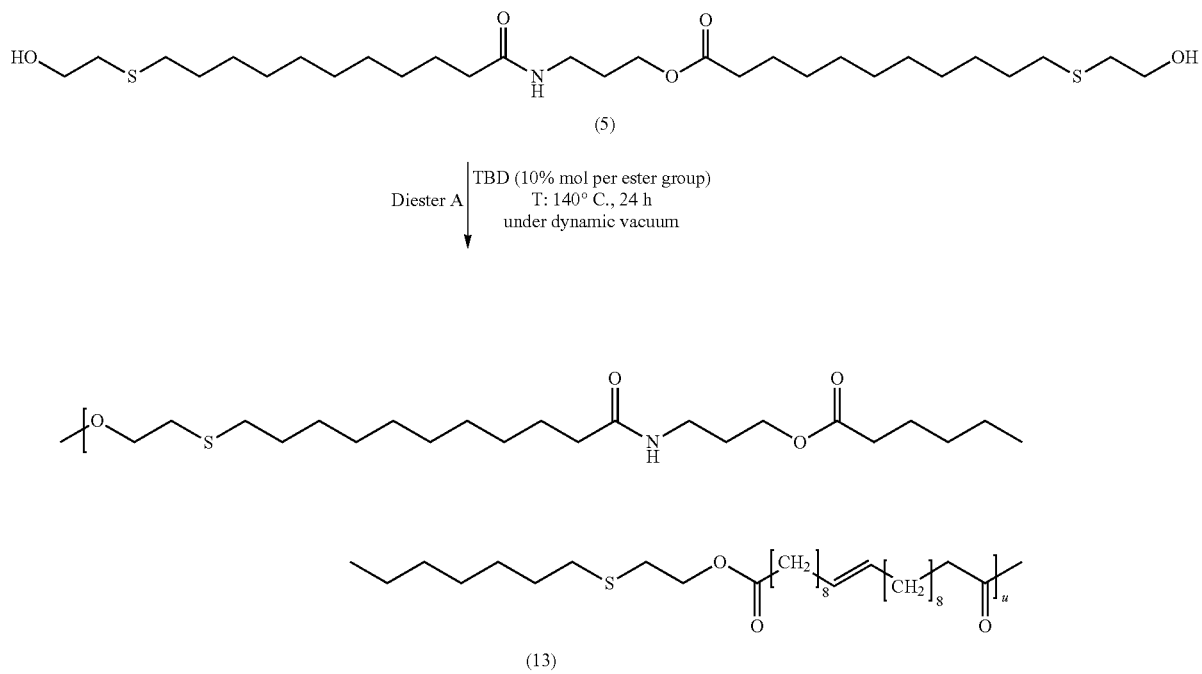

TABLE 4

Experimental results of polymerization

| Diester | $M_n{}^a$ | $M_w{}^a$ | $Đ^a$ | $T_g{}^b$ | $T_{m1}{}^b$ | $\Delta H_{m1}$ (J/g)$^b$ | $T_{m2}{}^b$ | $\Delta H_{m2}$ (J/g)$^b$ | $T_{5\%}{}^c$ |
|---|---|---|---|---|---|---|---|---|---|
| A | 17 547 | 33 071 | 1.8 | −40 | 48 | 43 | — | — | — |
| B | 12 308 | 22 873 | 1.8 | — | — | — | — | — | — |
| C | 4 619 | 9 665 | 2.1 | — | — | — | — | — | — |
| D | 4 555 | 7 378 | 1.6 | — | — | — | — | — | — |

$^a$SEC in THF PS standards
$^b$DSC 10° C./min
$^c$TGA after 5% degradation 10° C./min to 700° C.

Analysis

The products after the amidification and/or transesterification as well as after the thiolene reaction, were characterized with H and $^{13}$C-NMR, ATR-IR and DSC. The polymers made from compound (3) were analysed by GPC in THF, DSC, ATR-IR (polyurethanes) and TGA (polyesters).

$^1$H and $^{13}$C-NMR spectra were recorded using a Bruker AC-400 NMR at 70° C. or 50° C. by dissolving the samples respectively in CDCl$_3$ (compounds (5) and (7)) or DMSO (compound (3)). Size exclusion chromatography (SEC) analyses were performed at room temperature in THF with a setup consisting of a WATERS 880-PU pump and a series of three microstyragel columns with pore sizes of 103, 105 and 106 Å. The procedure to dissolve the sample was the following: 30 mg of the product was dissolved with 100 µL of dichloromethane and 100 µL of TFAA. After the complete solubilization 2 mL of THF was added and the sample was directly filtrated and injected. The elution of the filtered samples was monitored using refractive index detection. The elution times were converted to molar mass using a calibration curve based on low dispersity ($M_w/M_n$) polystyrene (PS) standards. Infrared spectra were obtained on a Bruker-Tensor 27 spectrometer using the attenuated total reflection (ATR) mode. Differential scanning calorimetry (DSC) thermograms were measured using a DSC Q100 apparatus from TA instruments.

Example 9

Preparation of Polymer (14) from Compound (3)

The synthesis of polymer (14) was performed at 180° C. under dynamic vacuum for 24 hours. The reaction was performed in presence of the catalyst Ti(OBu)$_4$. The polymer (14) was analyzed by SEC (Size Exclusion Chromatography) which indicates the following data: $M_n$=13 255 g/mol; and Dispersity: 1,6.

A DSC analysis has allowed to measure a $T_g$ of −28° C. and a $T_m$ of 109° C.

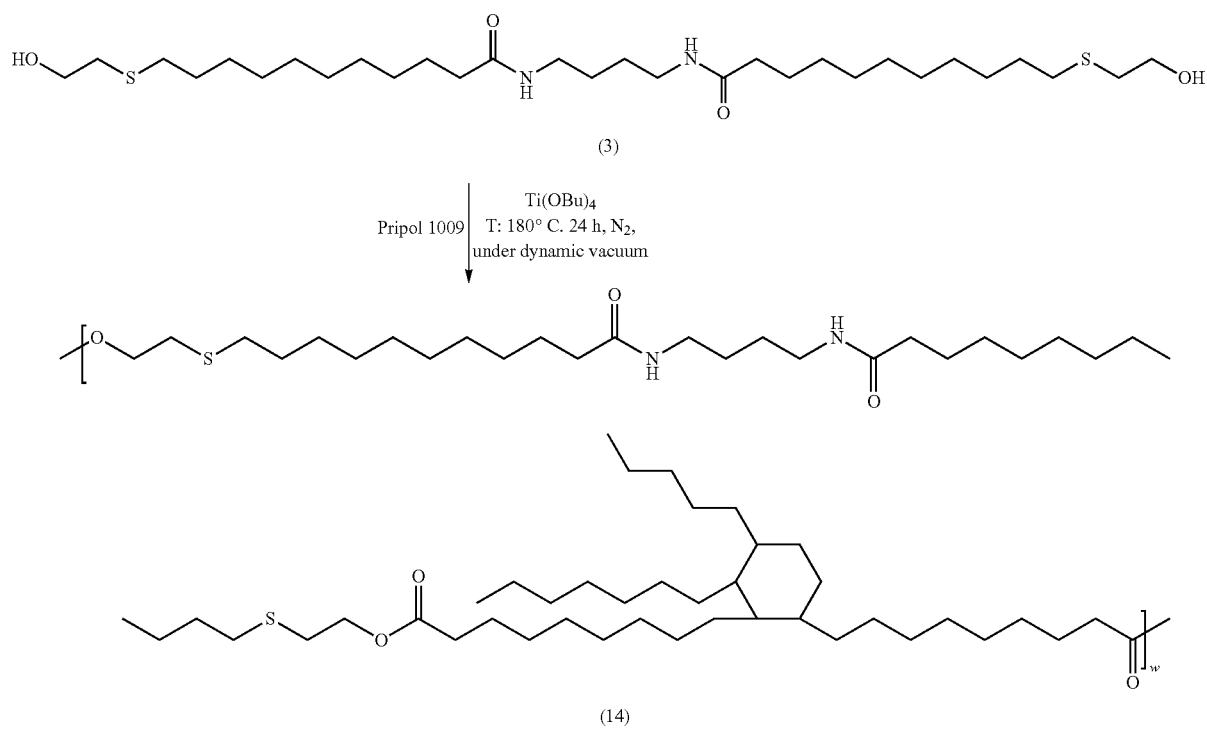

(3)

(14)

Binary mixtures of poly(ester-amide) (14) with PLLA (Poly(L-lactic acid)) was carried out by twin-screw extrusion at 180° C. The resulting products were analyzed by DSC, TGA and SEM in order to evaluate the morphology of the mixture as well as the thermo-mechanical properties.

For the DSC analysis, the sample was previously heated until a temperature of 190° C. at a heating rate of 10° C./min, then cooled down to −80° C. at a rate of 10° C./min. A second heating up to 190° C. allowed observing the different physical transitions of the material. Hence, a first slight endotherm near 50-60° C. was observed and highlights the glass transition of the PLA matrix. Such temperature does not vary with the proportion of the poly(ester-amide) (14) introduced in the material, which means that the mixture is non-miscible.

An exotherm was observed near 100-110° C. which demonstrates a cold crystallization of PLA. Such temperature decreases with the increase of the poly(ester-amide) (14) percentage in the material, which means that the compound (14) acts as nucleating agent of the PLA.

It was also observed that such crystallization happens when the poly(ester-amide) (14) melts.

At last, an endotherm at 170° C.-180° C. indicates the melting of the crystalline areas of the PLA.

The samples were also analyzed by DSC after annealing of 1 hour at 110° C. The disappearance of the cold crystallization of PLA was observed which highlights a total crystallization after annealing.

The degrees of crystallinity of the binary mixtures were measured:

| % by weight (14) | Degree of cristallinity $X_c$ (%) |
|---|---|
| 5 | 35 |
| 10 | 37 |

-continued

| % by weight (14) | Degree of cristallinity $X_c$ (%) |
|---|---|
| 15 | 37 |
| 20 | 41 |

A slight increase of the percentage of crystallinity of PLA was observed when the quantity of compound (14) in the mixture increases. Such observation confirms the aim of nucleating agent of the compound (14).

Such observation was confirmed with crystallization kinetics which were carried out with DSC. The samples were heated to 190° C. during 3 minutes in order to make all the crystalline areas of the material melt, then quickly cooled (50° C./min) to a temperature of 110° C.

Based on Avrami model, it was then possible to calculate the half-time of crystallization corresponding to the time necessary for reaching 50% of the whole crystallization of the PLA.

TABLE 5 half-time crystallization of PLLA in the binary mixtures

| Ratio PLA/compound (14) | $t_{1/2}$ (min) |
|---|---|
| 100/0 | 6.12 |
| 95/5 | 2.41 |
| 90/10 | 2.08 |
| 85/15 | 2.02 |
| 80/20 | 1.72 |

It is showed that the half-time crystallization highly decreases with the augmentation of the percentage weight of the compound (14) in the mixture. This confirms the nucleating aim of the compound (14) for PLA. Hence, the incorporation of compound (14) enhanced crystalline ability of PLA.

Moreover, traction tests were carried out on films of the mixtures. The constraint-deformation curves highlighted an increase in the elongation at break of the mixtures compared to pure PLLA which breaks at around 5%. An increase in the elongation at break in function of the percentage of compound (14) was observed until a value of 10%, then this maximal deformation decreased. A value of 250% was measured concerning the elongation at break of a binary mixture comprising 10% by weight of compound (14). The decreases of the maximal deformation after of percentage of 10% may be explained by heterogeneity of the size of the flexible nodules of compound (14) in the PLA matrix. Indeed, MEB analysis highlights a large dispersity of the nodule sizes of dispersed phase after 10%, which influences the cohesion of the mixture and thus the mechanical properties.

In conclusion, all theses analyses showed that the incorporation of compound (14) in PLLA matrix allows to increase the crystallization rate of PLLA, and also to increase the elongation at break during traction tests.

The invention claimed is:

1. A method of preparing a polyurethane, polyester or polyamide polymer comprising polymerizing a compound of formula (I):

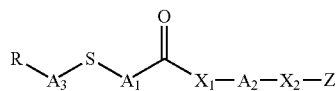

wherein:
R represents —OH or —NH$_2$;
A$_1$ represents a divalent alkylene radical, straight or branched, having from 2 to 20, and optionally comprising at least one double bond, and/or optionally substituted by at least one hydroxyl or amine group;
A$_2$ represents a divalent alkylene radical, straight or branched, having from 1 to 20, and optionally comprising at least one double bond and/or optionally substituted by at least one hydroxyl or amine group;
X$_1$ and X$_2$ represent, independently of each other, —NH— or —O—;
A$_3$ represents a divalent alkylene radical, straight or branched, having from 1 to 10, and optionally comprising at least one double bond and/or optionally substituted by at least one hydroxyl or amine group; and
Z represents a hydrogen or a group of formula (A'):

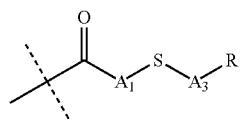

and wherein A$_1$, A$_3$ and R are as defined above in formula (I);
wherein said compound has the following formula (I-1):

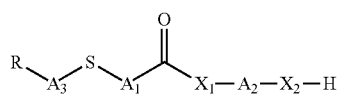

and wherein the compound is selected from the group consisting of:

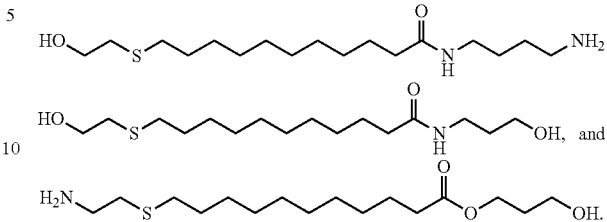

2. Compound having the following formula (I):

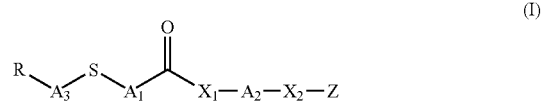

wherein:
R represents —OH or —NH$_2$;
A$_1$ represents a straight divalent alkylene radical, having from 3 to 20 carbon atoms, and optionally comprising at least one double bond, and/or optionally substituted by at least one hydroxyl or amine group;
A$_2$ represents a divalent alkylene radical, straight or branched, having from 3 to 20 carbon atoms, and optionally comprising at least one double bond, and/or optionally substituted by at least one hydroxyl or amine group;
X$_1$ and X$_2$ represent, independently of each other, —NH— or —O—;
A$_3$ represents a divalent alkylene radical, straight or branched, having from 1 to 10 carbon atoms, and optionally comprising at least one double bond, and/or optionally substituted by at least one hydroxyl or amine group;
Z represents a hydrogen or a group of formula (A'):

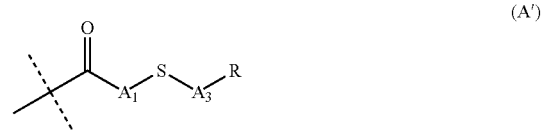

wherein A$_1$, A$_3$ and R are as defined above in formula (I);
and wherein when X$_1$ and X$_2$ represent —O—, then R represents —NH$_2$;
wherein said compound has the following formula (I-1):

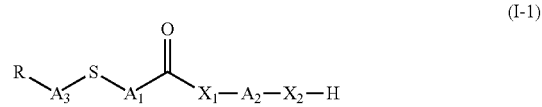

and wherein the compound is selected from the group consisting of:

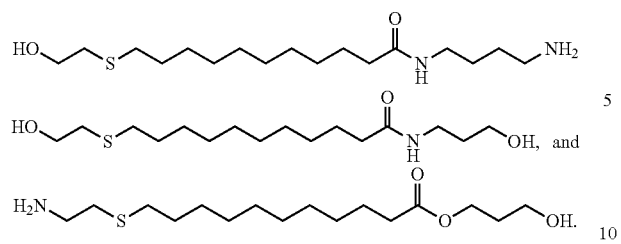

3. Compound having the following formula (I):

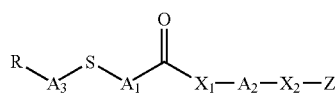

wherein:
- R represents —OH or —NH$_2$;
- A$_1$ represents a straight divalent alkylene radical, having from 3 to 20 carbon atoms, and optionally comprising at least one double bond, and/or optionally substituted by at least one hydroxyl or amine group;
- A$_2$ represents a divalent alkylene radical, straight or branched, having from 3 to 20 carbon atoms, and optionally comprising at least one double bond, and/or optionally substituted by at least one hydroxyl or amine group;
- X$_1$ and X$_2$ represent, independently of each other, —NH— or —O—;
- A$_3$ represents a divalent alkylene radical, straight or branched, having from 1 to 10 carbon atoms, and optionally comprising at least one double bond, and/or optionally substituted by at least one hydroxyl or amine group;
- Z represents a hydrogen or a group of formula (A'):

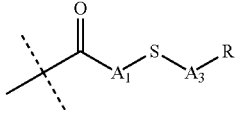

wherein A$_1$, A$_3$ and R are as defined above in formula (I);

and wherein when X$_1$ and X$_2$ represent —O—, then R represents —NH$_2$;

wherein the compound has the following formula (I-2):

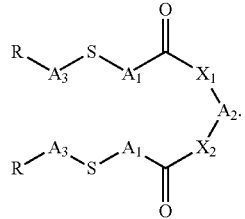

4. Compound according to claim 3, wherein the compound is selected from the group consisting of:

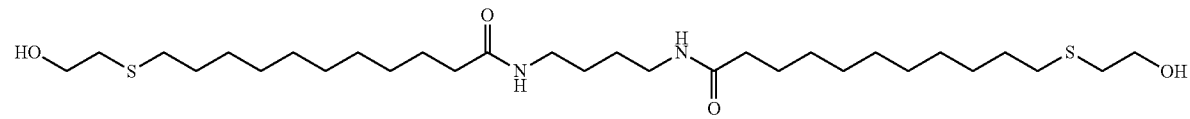

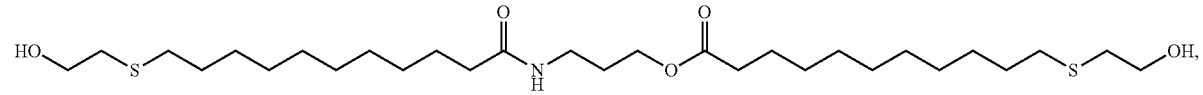

and

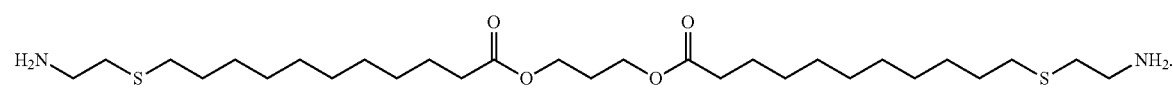

5. Polymer obtainable by polymerization of the compound of claim 2, and of a polyisocyanate.

6. Polymer according to claim 5, wherein the polyisocyanate is a diisocyanate of formula (O)CN-A$_4$-NC(O), wherein A$_4$ represents:
- an alkylene radical, straight or branched, having from 2 to 20 carbon atoms; or
- a cycloalkylene-alkylene-cycloalkylene radical, having from 6 to 30 carbon atoms; or
- a arylene-alkylene-arylene radical, having from 6 to 30 carbon atoms; or
- a cycloalkylene radical, having from 3 to 10 carbon atoms; or
- a alkylene-cycloalkylene, having from 3 to 15 carbon atoms; or
- an arylene radical, having from 6 to 10 carbon atoms, and wherein the alkylene, cycloalkylene and arylene radicals are optionally substituted by at least one substituent selected from the group consisting of alkyl, aryl and cycloalkyl.

7. Polymer according to claim 6, said polymer having the following formula (VII):

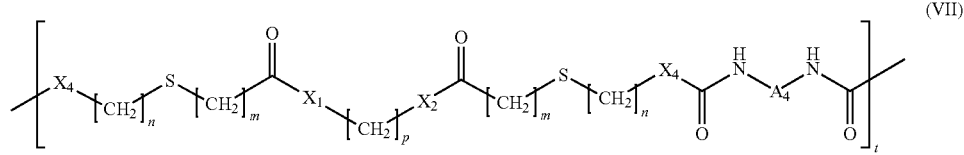

wherein:
- n is comprised from 1 to 10;
- m is comprised from 2 to 20;
- p is comprised from 1 to 20;
- X$_1$ and X$_2$ represent, independently of each other, —NH— or —O—;
- A$_4$ is as defined in claim 6;
- X$_4$ represents —NH— or —O—; and
- t represents a integer comprised from 1 to 50000.

8. Polymer obtainable by polymerization of the compound of claim 2, and of a polyester.

9. Polymer according to claim 8, wherein the polyester is a diester of formula (VI):

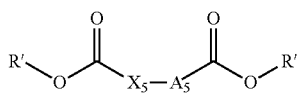

wherein:
- R' represents H, an alkyl group having from 1 to 10 carbon atoms, or a —C(O)R$_3$, R$_3$ being an alkyl group straight or branched, and having from 1 to 20 carbon atoms, and optionally comprising at least one double bond and/or optionally substituted by at least one hydroxyl or amine group;
- X$_5$ represents —CH$_2$— or —CH$_2$S—;
- A$_5$ represents an alkylene radical, straight or branched, having from 1 to 12 carbon atoms, said alkylene radical being eventually substituted by an alkyl group having from 1 to 10 carbon atoms, and said alkylene radical eventually comprising a double bond.

10. Polymer according to claim 8, said polymer having the following formula (VIII):

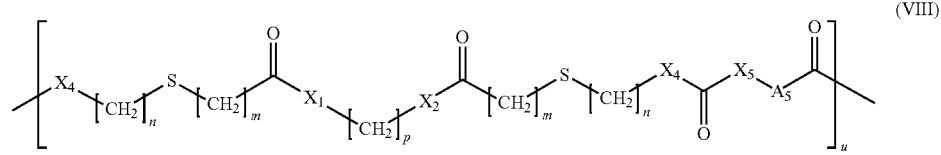

wherein:
- n is comprised from 1 to 10;
- m is comprised from 2 to 20;
- p is comprised from 1 to 20;
- X$_1$ and X$_2$ represent, independently of each other, —NH— or —O—;
- X$_5$ represents —CH$_2$— or —CH$_2$S—;
- A$_5$ represents represents an alkylene radical, straight or branched, having from 1 to 12 carbon atoms, said alkylene radical being eventually substituted by an alkyl group having from 1 to 10 carbon atoms, and said alkylene radical eventually comprising a double bond;
- X$_4$ represents —NH— or —O—; and
- u represents a integer comprised from 1 to 50000.

11. Process for preparing the compound of formula (I) as defined in claim 2, said process comprising the following steps:
a) reacting a compound of formula (II):

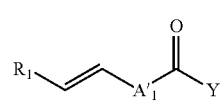

wherein
- A'$_1$ represents a bond or a divalent alkylene radical, straight or branched, having from 1 to 18 carbon atoms, said alkylene radical optionally comprising at least a double bond, and/or optionally substituted by at least one hydroxyl or amine group;
- R$_1$ being a hydrogen or an alkyl group, straight or branched, having from 1 to 15 carbon atoms;
- Y represents —OR$_2$ or —X;
- X being a halogen;

R$_2$ being a hydrogen, an alkyl group, straight or branched, having from 1 to 10 carbon atoms, or a —(C═O)R$_3$, R$_3$ being an alkyl group straight or branched, and having from 1 to 20 carbon atoms, and optionally comprising at least one double bond and/or optionally substituted by at least one hydroxyl or amine group;

with a compound of formula (III): H —X$_1$-A$_2$-X$_2$—H (III), A$_2$ being as defined above in formula (I), to obtain a compound of formula (IV):

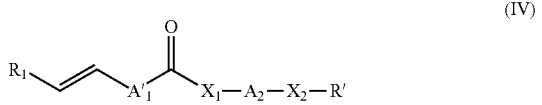

(IV)

wherein:
A$_2$ represents a divalent alkylene radical, straight or branched, having from 1 to 20, and optionally comprising at least one double bond, and/or optionally substituted by at least one hydroxyl or amine group;
X$_1$ and X$_2$ represent, independently of each other, —NH— or —O—;
R$_1$ and A'$_1$ are as defined above in formula (II);
R' represents a hydrogen atom or a group of formula (A"):

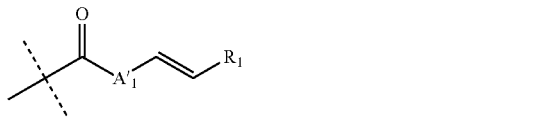

A'$_1$ and R$_1$ being as defined above in formula (II),
b) conducting a thiolene reaction of the compound of formula (IV) resulting from step a) as defined above, with a thiol of formula (V):

HS-A$_3$-X$_3$  (V)

wherein A$_3$ represents a divalent alkylene radical, straight or branched, having from 1 to 10, and optionally comprising at least one double bond and/or optionally substituted by at least one hydroxyl or amine group;
and X$_3$ represents either —OH or —NH$_3$$^+$Cl$^-$; and
c) optionally having a step of basic treatment of the compound resulting from step b);
for obtaining the compound of formula (I).

12. Process according to claim 11, for the preparation of a compound of formula

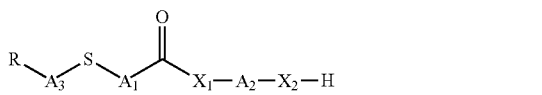

wherein:
R represents —OH or —NH$_2$;
A$_1$ represents a divalent alkylene radical, straight or branched, having from 3 to 20 carbon atoms, and optionally comprising at least one double bond, and/or optionally substituted by at least one hydroxyl or amine group;
A$_2$ represents a divalent alkylene radical, straight or branched, having from 3 to 20 carbon atoms, and optionally comprising at least one double bond, and/or optionally substituted by at least one hydroxyl or amine group;
X$_1$ and X$_2$ represent, independently of each other, —NH— or —O—;
A$_3$ represents a divalent alkylene radical, straight or branched, having from 1 to 10, carbon atoms, and optionally comprising at least one double bond, and/or optionally substituted by at least one hydroxyl or amine group;
wherein the step a) of said process leads to a compound of formula (IV) wherein R' represents H.

13. Process according to claim 11, for the preparation of a compound of formula (I-2)

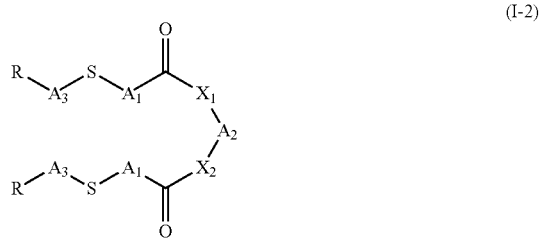

(I-2)

wherein:
A$_1$ represents a divalent alkylene radical, straight or branched, having from 3 to 20 carbon atoms, and optionally comprising at least one double bond, and/or optionally substituted by at least one hydroxyl or amine group;
A$_2$ represents a divalent alkylene radical, straight or branched, having from 3 to 20 carbon atoms, and optionally comprising at least one double bond, and/or optionally substituted by at least one hydroxyl or amine group;
X$_1$ and X$_2$ represent, independently of each other, —NH— or —O—;
A$_3$ represents a divalent alkylene radical, straight or branched, having from 1 to 10, carbon atoms, and optionally comprising at least one double bond, and/or optionally substituted by at least one hydroxyl or amine group;
wherein the step a) of said process leads to a compound of formula (IV) wherein R' represents a group of formula (A") as defined in claim 11.

14. A method for the preparation of adhesives, surfactants, coatings, packing, paints, fibers, foams, or products in the cosmetic or medical fields, comprising forming the polymer of claim 5 into an adhesive, surfactant, coating, packing, paint, fiber, foam, or product in the cosmetic or medical fields.

15. Polymer obtainable by polymerization of the compound of claim 2, and of a diacid derivative selected from the group consisting of diacid, diester and dianhydride compounds.

16. Polymer according to claim 15, wherein the diacid derivative has the following formula (XI):

R'''OOC—R"—COOR'''  (XI)

wherein R" represents:
an alkyl radical, straight or branched, having from 1 to 30 carbon atoms; or
an alkylene-cycloalkylene-alkylene radical, having from 6 to 50 carbon atoms; or a cycloalkylene radical having from 6 to 30 carbon atoms,
an arylene radical having from 6 to 30 carbon atoms; or
a polymer;
wherein R''' represents H, an alkyl group as defined above or an anhydride group (COAlk, Alk representing an alkyl group as defined above),
wherein the alkylene, cycloalkylene and arylene radicals are:
optionally substituted by at least one substituent selected from the group consisting of alkyl, aryl and cycloalkyl; and/or
optionally interrupted with at least one heteroatom selected from the group consisting of O, N and S.

17. Polymer obtainable by polymerization of the compound of claim 2, and of a diacid.

18. Polymer according to claim 17, wherein the diacid has the following formula (XI):

HOOC—R''—COOH            (XI)

wherein R'' represents:
an alkylene radical, straight or branched, having from 1 to 30 carbon atoms; or
an alkylene-cycloalkylene-alkylene radical, having from 6 to 50 carbon atoms; or
a cycloalkylene radical having from 6 to 30 carbon atoms,
an arylene radical having from 6 to 30 carbon atoms; or
a polymer;
wherein the alkylene, cycloalkylene and arylene radicals are:
optionally substituted by at least one substituent selected from the group consisting of alkyl, aryl and cycloalkyl; and/or
optionally interrupted with at least one heteroatom selected from the group consisting of O, N and S.

19. Polymer according to claim 17, said polymer having the formula (IX) or (X):

$A_2$ represents a divalent alkylene radical, straight or branched, having from 3 to 20 carbon atoms, and optionally comprising at least one double bond, and/or optionally substituted by at least one hydroxyl or amine group;

$X_1$ and $X_2$ represent, independently of each other, —NH— or —O—;

$A_3$ represents a divalent alkylene radical, straight or branched, having from 1 to 10, carbon atoms, and optionally comprising at least one double bond, and/or optionally substituted by at least one hydroxyl or amine group; $X_7$ represents —O— or —NH—;

$X_6$ represents —O— or —NH—;

v and w, independently of each other, represent a integer comprised from 1 to 50000;

R'' represents:
an alkylene radical, straight or branched, having from 1 to 30 carbon atoms; or an alkylene-cycloalkylene-alkylene radical, having from 6 to 50 carbon atoms; or a cycloalkylene radical having from 6 to 30 carbon atoms, an arylene radical having from 6 to 30 carbon atoms; or
a polymer;
wherein the alkylene, cycloalkylene and arylene radicals are:

(IX)

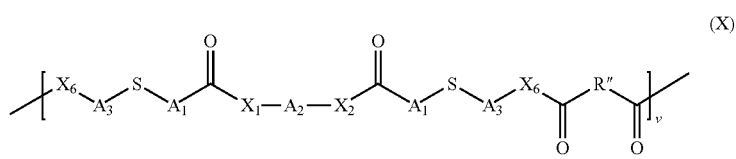
(X)

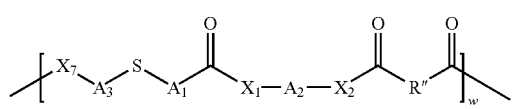

wherein:

$A_1$ represents a divalent alkylene radical, straight or branched, having from 3 to 20 carbon atoms, and optionally comprising at least one double bond, and/or optionally substituted by at least one hydroxyl or amine group;

optionally substituted by at least one substituent selected from the group consisting of alkyl, aryl and cycloalkyl; and/or
optionally interrupted with at least one heteroatom selected from the group consisting of O, N and S.

20. Polymer according to claim 7, where the diester is selected from the group consisting of:

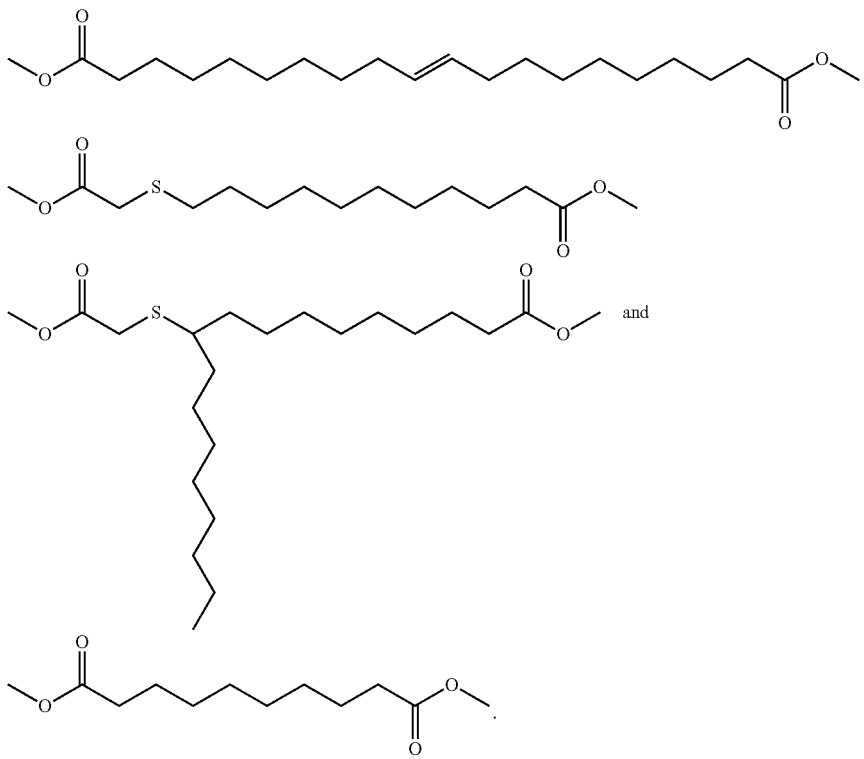

21. A method of preparing a polyurethane, polyester or polyamide polymer comprising polymerizing a compound of formula (I):

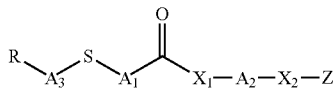
(I)

wherein:
R represents —OH or —NH$_2$;
A$_1$ represents a divalent alkylene radical, straight or branched, having from 2 to 20, and optionally comprising at least one double bond, and/or optionally substituted by at least one hydroxyl or amine group;
A$_2$ represents a divalent alkylene radical, straight or branched, having from 1 to 20, and optionally comprising at least one double bond and/or optionally substituted by at least one hydroxyl or amine group;
X$_1$ and X$_2$ represent, independently of each other, —NH— or —O—;
A$_3$ represents a divalent alkylene radical, straight or branched, having from 1 to 10, and optionally comprising at least one double bond and/or optionally substituted by at least one hydroxyl or amine group; and
Z represents a hydrogen or a group of formula (A'):

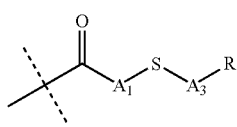
(A')

and wherein A$_1$, A$_3$ and R are as defined above in formula (I);
wherein the compound has the following formula (I-2):

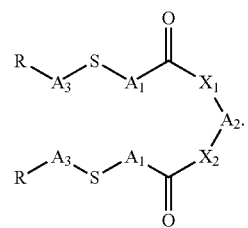
(I-2)

22. Polymer obtainable by polymerization of the compound of claim 3, and of a polyisocyanate.

23. Polymer according to claim 22, wherein the polyisocyanate is a diisocyanate of formula (O)CN—A$_4$—NC(O), wherein A$_4$ represents:
an alkylene radical, straight or branched, having from 2 to 20 carbon atoms; or
a cycloalkylene-alkylene-cycloalkylene radical, having from 6 to 30 carbon atoms; or
a arylene-alkylene-arylene radical, having from 6 to 30 carbon atoms; or
a cycloalkylene radical, having from 3 to 10 carbon atoms; or
a alkylene-cycloalkylene, having from 3 to 15 carbon atoms; or
an arylene radical, having from 6 to 10 carbon atoms,
and wherein the alkylene, cycloalkylene and arylene radicals are optionally substituted by at least one substituent selected from the group consisting of alkyl, aryl and cycloalkyl.

24. Polymer according to claim 23, said polymer having the following formula (VII):

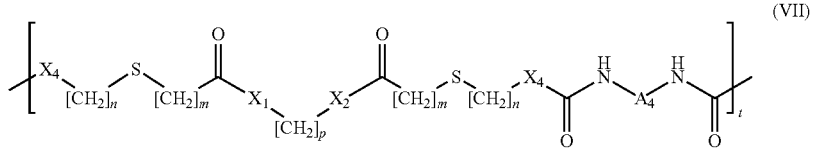

wherein:
n is comprised from 1 to 10;
m is comprised from 2 to 20;
p is comprised from 1 to 20;
$X_1$ and $X_2$ represent, independently of each other, —NH— or —O—;
$A_4$ is as defined in claim 8;
$X_4$ represents —NH— or —O—; and
t represents a integer comprised from 1 to 50000.

25. Polymer obtainable by polymerization of the compound of claim 3, and of a polyester.

26. Polymer according to claim 25, wherein the polyester is a diester of formula (VI):

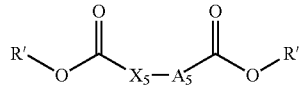

wherein:
R' represents H, an alkyl group having from 1 to 10 carbon atoms, or a —C(O)$R_3$, $R_3$ being an alkyl group straight or branched, and having from 1 to 20 carbon atoms, and optionally comprising at least one double bond and/or optionally substituted by at least one hydroxyl or amine group;
$X_5$ represents —$CH_2$— or —$CH_2S$—;
$A_5$ represents an alkylene radical, straight or branched, having from 1 to 12 carbon atoms, said alkylene radical being eventually substituted by an alkyl group having from 1 to 10 carbon atoms, and said alkylene radical eventually comprising a double bond.

27. Polymer according to claim 25, said polymer having the following formula (VIII):

$X_1$ and $X_2$ represent, independently of each other, —NH— or —O—;
$X_5$ represents —$CH_2$— or —$CH_2S$—;

$A_5$ represents represents an alkylene radical, straight or branched, having from 1 to 12 carbon atoms, said alkylene radical being eventually substituted by an alkyl group having from 1 to 10 carbon atoms, and said alkylene radical eventually comprising a double bond; $X_4$ represents —NH— or —O—; and u represents a integer comprised from 1 to 50000.

28. Process for preparing the compound of formula (I) as defined in claim 5, said process comprising the following steps:

c) reacting a compound of formula (II):

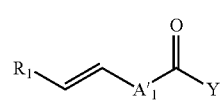

wherein $A'_1$ represents a bond or a divalent alkylene radical, straight or branched, having from 1 to 18 carbon atoms, said alkylene radical optionally comprising at least a double bond, and/or optionally substituted by at least one hydroxyl or amine group;

$R_1$ being a hydrogen or an alkyl group, straight or branched, having from 1 to 15 carbon atoms;

Y represents —$OR_2$ or —X;

X being a halogen;

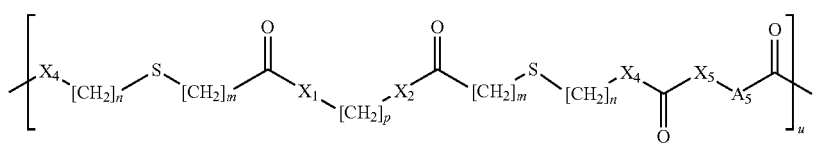

wherein:
n is comprised from 1 to 10;
m is comprised from 2 to 20;
p is comprised from 1 to 20;

$R_2$ being a hydrogen, an alkyl group, straight or branched, having from 1 to 10 carbon atoms, or a —(C=O)$R_3$, $R_3$ being an alkyl group straight or branched, and having from 1 to 20 carbon atoms, and optionally comprising at least one double bond and/or optionally substituted by at least one hydroxyl or amine group;

with a compound of formula (III): H—$X_1$—$A_2$—$X_2$—H (III), $A_2$ being as defined above in formula (I), to obtain a compound of formula (IV):

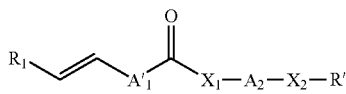
(IV)

wherein:
- $A_2$ represents a divalent alkylene radical, straight or branched, having from 1 to 20, and optionally comprising at least one double bond, and/or optionally substituted by at least one hydroxyl or amine group;
$X_1$ and $X_2$ represent, independently of each other, —NH— or —O—;
$R_1$ and $A'_1$ are as defined above in formula (II);
R' represents a hydrogen atom or a group of formula (A"):

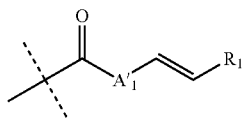

$A'_1$ and $R_1$ being as defined above in formula (II),
d) conducting a thiolene reaction of the compound of formula (IV) resulting from step a) as defined above, with a thiol of formula (V):

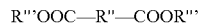
HS—$A_3$—$X_3$ (V)

wherein $A_3$ represents a divalent alkylene radical, straight or branched, having from 1 to 10, and optionally comprising at least one double bond and/or optionally substituted by at least one hydroxyl or amine group; and $X_3$ represents either —OH or —$NH_3^+C^-$; and c) optionally having a step of basic treatment of the compound resulting from step b);

for obtaining the compound of formula (I).

29. Process according to claim 28, for the preparation of a compound of formula (I-2)

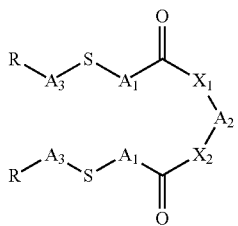
(I-2)

wherein:
$A_l$ represents a divalent alkylene radical, straight or branched, having from 3 to 20 carbon atoms, and optionally comprising at least one double bond, and/or optionally substituted by at least one hydroxyl or amine group;

$A_2$ represents a divalent alkylene radical, straight or branched, having from 3 to 20 carbon atoms, and optionally comprising at least one double bond, and/or optionally substituted by at least one hydroxyl or amine group;

$X_1$ and $X_2$ represent, independently of each other, —NH— or —O—;

$A_3$ represents a divalent alkylene radical, straight or branched, having from 1 to 10, carbon atoms, and optionally comprising at least one double bond, and/or optionally substituted by at least one hydroxyl or amine group;

wherein the step a) of said process leads to a compound of formula (IV) wherein R' represents a group of formula (A") as defined in claim 13.

30. A method for the preparation of adhesives, surfactants, coatings, packing, paints, fibers, foams, or products in the cosmetic or medical fields, comprising forming the polymer of claim 22 into an adhesive, surfactant, coating, packing, paint, fiber, foam, or product in the cosmetic or medical fields.

31. Polymer obtainable by polymerization of the compound of claim 3, and of a diacid derivative selected from the group consisting of diacid, diester and dianhydride compounds.

32. Polymer according to claim 31, wherein the diacid derivative has the following formula (XI):

R'''OOC—R"—COOR''' (XI)

wherein R" represents:
an alkylene radical, straight or branched, having from 1 to 30 carbon atoms; or
an alkylene-cycloalkylene-alkylene radical, having from 6 to 50 carbon atoms; or
a cycloalkylene radical having from 6 to 30 carbon atoms,
an arylene radical having from 6 to 30 carbon atoms; or
a polymer;
wherein R''' represents H, an alkyl group as defined above or an anhydride group (COAlk, Alk representing an alkyl group as defined above),
wherein the alkylene, cycloalkylene and arylene radicals are:
optionally substituted by at least one substituent selected from the group consisting of alkyl, aryl and cycloalkyl; and/or
optionally interrupted with at least one heteroatom selected from the group consisting of O, N and S.

33. Polymer obtainable by polymerization of the compound of claim 3, and of a diacid.

34. Polymer according to claim 33, wherein the diacid has the following formula (XI):

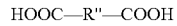
HOOC—R"—COOH (XI)

wherein R" represents:
an alkylene radical, straight or branched, having from 1 to 30 carbon atoms; or
an alkylene-cycloalkylene-alkylene radical, having from 6 to 50 carbon atoms; or
a cycloalkylene radical having from 6 to 30 carbon atoms,
an arylene radical having from 6 to 30 carbon atoms; or
a polymer;
wherein the alkylene, cycloalkylene and arylene radicals are:

optionally substituted by at least one substituent selected from the group consisting of alkyl, aryl and cycloalkyl; and/or optionally interrupted with at least one heteroatom selected from the group consisting of O, N and S.

35. Polymer according to claim 33, said polymer having the formula (IX) or (X):

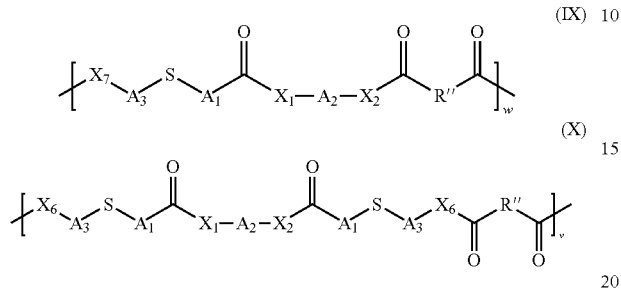

wherein:

- $A_l$ represents a divalent alkylene radical, straight or branched, having from 3 to 20 carbon atoms, and optionally comprising at least one double bond, and/or optionally substituted by at least one hydroxyl or amine group;
- $A_2$ represents a divalent alkylene radical, straight or branched, having from 3 to 20 carbon atoms, and optionally comprising at least one double bond, and/or optionally substituted by at least one hydroxyl or amine group;
- $X_1$ and $X_2$ represent, independently of each other, —NH— or —O—;
- $A_3$ represents a divalent alkylene radical, straight or branched, having from 1 to 10, carbon atoms, and optionally comprising at least one double bond, and/or optionally substituted by at least one hydroxyl or amine group; $X_7$ represents —O— or —NH—;
- $X_6$ represents —O— or —NH—;
- v and w, independently of each other, represent a integer comprised from 1 to 50000;
- R" represents:
    - an alkylene radical, straight or branched, having from 1 to 30 carbon atoms; or
    - an alkylene-cycloalkylene-alkylene radical, having from 6 to 50 carbon atoms,; or
    - a cycloalkylene radical having from 6 to 30 carbon atoms,
    - an arylene radical having from 6 to 30 carbon atoms; or
    - a polymer;

wherein the alkylene, cycloalkylene and arylene radicals are:

- optionally substituted by at least one substituent selected from the group consisting of alkyl, aryl and cycloalkyl; and/or
- optionally interrupted with at least one heteroatom selected from the group consisting of O, N and S.

36. Polymer according to claim 26, where the diester is selected from the group consisting of:

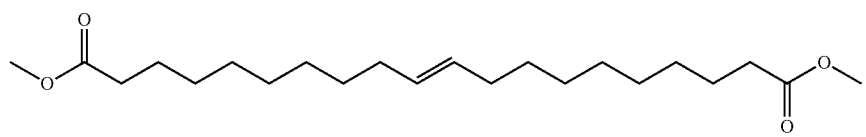

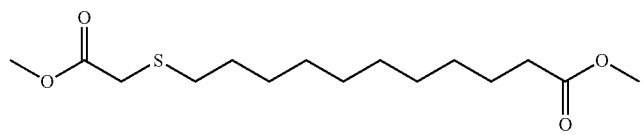

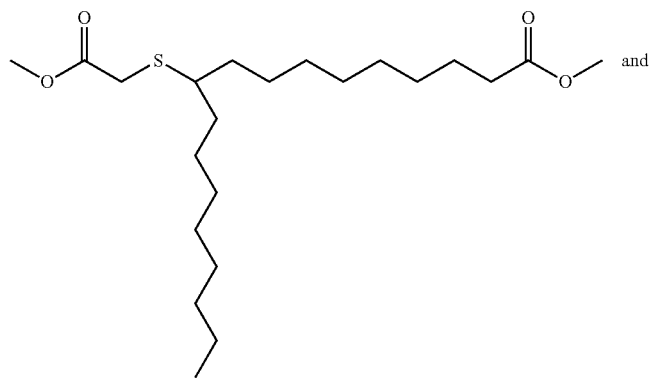

and

-continued
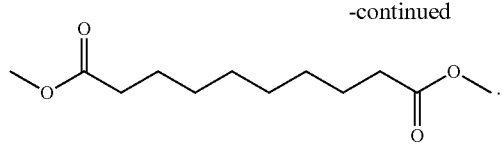
37. Process according to claim 11, where X is a chlorine atom.
38. Process according to claim 28, where X is a chlorine atom.
* * * * *